US008791253B2

(12) United States Patent
Prakash et al.

(10) Patent No.: US 8,791,253 B2
(45) Date of Patent: *Jul. 29, 2014

(54) REBAUDIOSIDE A COMPOSITION AND METHOD FOR PURIFYING REBAUDIOSIDE A

(75) Inventors: Indra Prakash, Alpharetta, GA (US); Grant E. DuBois, Roswell, GA (US); George A. King, Atlanta, GA (US); Mani Upreti, Dunwoody, GA (US)

(73) Assignee: The Coca-Cola Company, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/751,627

(22) Filed: May 21, 2007

(65) Prior Publication Data

US 2007/0292582 A1    Dec. 20, 2007

Related U.S. Application Data

(60) Provisional application No. 60/889,318, filed on Feb. 12, 2007, provisional application No. 60/805,216, filed on Jun. 19, 2006.

(51) Int. Cl.
*C07H 1/06* (2006.01)
*C07H 1/08* (2006.01)
*A23L 1/236* (2006.01)

(52) U.S. Cl.
USPC ........................................ 536/128; 426/548

(58) Field of Classification Search
CPC ................................. C07H 1/08; A23L 1/236
USPC ........................................ 536/128; 426/548
See application file for complete search history.

(56) References Cited

U.S. PATENT DOCUMENTS

| 3,723,410 | A | 3/1973 | Persinos |
| 4,082,858 | A | 4/1978 | Morita et al. |
| 4,188,390 | A | 2/1980 | Campbell et al. |
| 4,206,222 | A | 6/1980 | Valetas et al. |
| 4,219,571 | A | 8/1980 | Miyake |
| 4,332,830 | A | 6/1982 | DuBois |
| 4,353,889 | A | 10/1982 | DuBois |
| 4,361,697 | A | 11/1982 | Dobberstein et al. |
| 4,381,402 | A | 4/1983 | DuBois |
| 4,402,990 | A | 9/1983 | DuBois |
| 4,404,367 | A | 9/1983 | DuBois |
| 4,454,290 | A | 6/1984 | DuBois |
| 4,515,785 | A | 5/1985 | Shimizu et al. |
| 4,590,160 | A | 5/1986 | Nishihashi et al. |
| 4,599,403 | A | 7/1986 | Kumar |
| 5,112,610 | A | 5/1992 | Kienle |
| 5,530,106 | A | 6/1996 | Navia et al. |
| PP10,562 | P | 8/1998 | Sys et al. |
| PP10,563 | P | 8/1998 | Brandle et al. |
| PP10,564 | P | 8/1998 | Marsolais et al. |
| 5,962,678 | A | 10/1999 | Payzant et al. |
| 5,972,120 | A | 10/1999 | Kutowy et al. |
| 6,255,557 | B1 | 7/2001 | Brandle |
| 6,331,646 | B1 | 12/2001 | Schroeder et al. |
| 6,423,864 | B1 | 7/2002 | Prakash et al. |
| 6,784,309 | B2 | 8/2004 | Prakash et al. |
| 6,809,198 | B2 | 10/2004 | El Kabbani et al. |
| 6,998,480 | B2 | 2/2006 | Catani et al. |
| 7,049,435 | B2 | 5/2006 | Catani et al. |
| 2002/0065245 | A1 | 5/2002 | Brouwers |
| 2003/0138538 | A1 | 7/2003 | Kitazume et al. |
| 2004/0030124 | A1 | 2/2004 | Catani et al. |
| 2005/0010040 | A1 | 1/2005 | Gourdin et al. |
| 2006/0083838 | A1 | 4/2006 | Jackson et al. |
| 2006/0134292 | A1 | 6/2006 | Abelyan et al. |
| 2006/0142555 | A1 | 6/2006 | Jonnala et al. |
| 2007/0082102 | A1 | 4/2007 | Magomet et al. |
| 2007/0082103 | A1 | 4/2007 | Magomet et al. |
| 2007/0116800 | A1 | 5/2007 | Prakash et al. |
| 2007/0116819 | A1 | 5/2007 | Prakash et al. |
| 2007/0116820 | A1 | 5/2007 | Prakash et al. |
| 2007/0116821 | A1 | 5/2007 | Prakash et al. |
| 2007/0116822 | A1 | 5/2007 | Prakash et al. |
| 2007/0116823 | A1 | 5/2007 | Prakash et al. |
| 2007/0116824 | A1 | 5/2007 | Prakash et al. |
| 2007/0116825 | A1 | 5/2007 | Prakash et al. |
| 2007/0116826 | A1 | 5/2007 | Prakash et al. |

(Continued)

FOREIGN PATENT DOCUMENTS

| CA | 2278083 | 1/2001 |
| EP | 1407679 | 4/2004 |

(Continued)

OTHER PUBLICATIONS

Kolář, P. Shen, J.-W., Tsuboi, A., Ishikawa, T. (2002) Solvent selection for pharmaceuticals. Fluid Phase Equilibria, vol. 194-197, p. 771-782.*
"2.2 Recrystallization" [online], [retrieved Dec. 10, 2009]. Published on the internet Sep. 12, 2003. Retrieved from the internet <http://siggy.chem.ucla.edu/VOH/136/Recrystallization.pdf>.*
Nass, K.K. (1994) Rational Solvent Selection for Cooling Crystallizations. Industrial & Engineering Chemistry Reseach, vol. 33, p. 1580-1584.*
Kojima, S. (1997) ICH Guideline for Residual Solvents (Q3C) in Proceedings of the 4th International Conference on Harmonization of Technical Requirements for Registration of Pharmaceuticals, Brussels, Belgium, Jul. 16-18, 1997. Retrieved from the internet [Apr. 2, 2010] from <http://www.nihs.go.jp/drug/ich_q3c_step4/q3cdrf_9.html#6>.*

(Continued)

*Primary Examiner* — Scarlett Goon
(74) *Attorney, Agent, or Firm* — King & Spalding

(57) ABSTRACT

Exemplary embodiments of this invention encompass a method for purifying crude rebaudioside A. In particular, this invention relates to a method for purifying crude rebaudioside A compositions comprising purities from approximately 40% to approximately 95% rebaudioside A to obtain a substantially pure rebaudioside A product with a single crystallization step. Resulting polymorph and amorphous forms of rebaudioside A and methods for preparing polymorph and amorphous forms of rebaudioside A from crude rebaudioside A compositions and substantially pure rebaudioside A compositions also are disclosed.

15 Claims, 11 Drawing Sheets

(56) References Cited

U.S. PATENT DOCUMENTS

| | | |
|---|---|---|
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0128311 A1 | 6/2007 | Prakash et al. |
| 2007/0134390 A1 | 6/2007 | Prakash et al. |
| 2007/0134391 A1 | 6/2007 | Prakash et al. |
| 2010/0137569 A1 | 6/2010 | Prakash et al. |

FOREIGN PATENT DOCUMENTS

| | | |
|---|---|---|
| JP | 52062300 | 5/1977 |
| JP | 56121453 | 9/1981 |
| JP | 56121455 | 9/1981 |
| JP | 57086264 A | 5/1982 |
| JP | 59071662 A | 4/1984 |
| JP | 59120073 A | 7/1984 |
| JP | 60027360 A | 2/1985 |
| JP | 60037950 A | 2/1985 |
| JP | 62091161 A | 4/1985 |
| WO | 00/32621 | 6/2000 |
| WO | 00/52019 | 9/2000 |
| WO | WO 2006/038221 | 4/2006 |
| WO | WO 2007149672 A2 | 12/2007 |
| WO | WO 2008147725 A1 | 12/2008 |
| WO | WO 2011082288 A1 | 7/2011 |

OTHER PUBLICATIONS

"Alcohol, Chemistry and You" by Dr. Bill Boggan from ChemCases. Com Edition [online], [retrieved Oct. 18, 2010]. Retrieved from the internet <http://web.archive.org/web/20011003192033/http://chemcases.com/alcohol/alc-03.htm> Available on Oct. 3, 2001.*

"Denatured Alcohol MSDS" from PTI Process Chemicals [online], [retrieved Oct. 18, 2010]. Retrieved from the internet <http://www.ptichem.com/MSDS%20Sheets/Ethyl%20MSDS.htm> Published Apr. 25, 2005.*

Shibata et al., Glucosylation of Steviol and Steviol-Glucosides in Extracts from *Stevia rebaudiana* Bertoni, Plant Physiol. 95: 152-156 (1991).

Zell et al., Tetrahedron 56(36) 6603-16 (2000).

Hancock, B.C. and Parks, M., "What is the True Solubility Advantage for Amorphous Pharmaceuticals," *Pharmaceuticals Research* vol. 17, No. 4, pp. 397-404 (2000).

Luft, J.R., et al., "Efficient optimization of crystallization conditions by manipulation of drop volume and temperature," *Protein Science* vol. 16, No. 4, pp. 715-722 (2007).

Mullin, J.W., "Industrial Crystallization" in *Crystallization*, Butterworth Inc., pp. 158-169 (1961).

Bonomelli, Federico, "International Search Report and Written Opinion of the International Searching Authority", Oct. 14, 2008, PCT/US2008/063845, European Patent Office, Rijswijk, The Netherlands.

Lombart, Isabelle, "International Search Report and Written Opinion of the International Searching Authority", Mar. 22, 2011, PCT/US2010/062479, European Patent Office, Rijswijk, The Netherlands.

Third Party Submission for U.S. Appl. No. 11/751,627, (Jun. 26, 2012).

* cited by examiner

REBAUDIOSIDE A COMPOSITION AND METHOD FOR PURIFYING REBAUDIOSIDE A

RELATED APPLICATION DATA

The present application claims priority under 35 U.S.C. §119(e) to U.S. Provisional Application Nos. 60/805,216, filed on Jun. 19, 2006, and 60/889,318, filed on Feb. 12, 2007, both entitled "Rebaudioside A Composition and Method for Purifying Rebaudioside A." The disclosures of these applications are hereby incorporated by reference in their entirety.

FIELD OF INVENTION

This invention relates generally to polymorphic and amorphous forms of rebaudioside A, methods for purifying rebaudioside A, and methods for preparing polymorphic and amorphous forms of rebaudioside A. More particularly, this invention relates to polymorphic and amorphous forms of rebaudioside A and methods for the purification or crystallization of rebaudioside A with aqueous organic solvents or organic solvents to obtain a product in high yield and high purity.

BACKGROUND OF INVENTION

Rebaudioside A is a high-potency diterpenoid glycoside sweetener having the chemical structure:

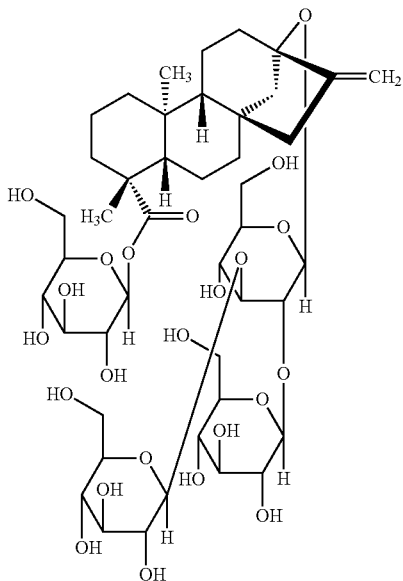

Rebaudioside A is isolated and extracted, along with other steviol glycosides, from the *Stevia rebaudiana* (Bertoni) plant ("*Stevia*"), which is commercially cultivated in Japan, Singapore, Taiwan, Malaysia, South Korea, China, Israel, India, Brazil, Australia, and Paraguay. It is an alternative non-caloric sweetener with functional and sensory properties superior to those of many high-potency sweeteners. Processed forms of *Stevia* can be 70 to 400 times more potent than sugar; however, *Stevia* also has a bitter component. Of the four major diterpenoid glycoside sweeteners present in *Stevia*, rebaudioside A has been identified as the least bitter, and with the least persistent aftertaste. Bitterness often is significantly due to the impurities in extracts.

Rebaudioside A is generally available at ≤80% pure. The primary impurities comprise stevioside, steviolbioside, rebaudioside B, rebaudioside C, rebaudioside D, dulcoside A, rebaudioside F, and other steviol glycosides. It is very difficult to obtain a high purity of rebaudioside A in high recovery because the rebaudioside A and the impurities have similar solubilities.

Previously reported efforts to purify rebaudioside A from mixtures of rebaudioside A and stevioside require numerous repeated purification steps. U.S. Pat. No. 5,962,678 discloses the re-crystallization of rebaudioside A using an anhydrous methanol solution to obtain an 80% pure rebaudioside A. By repeating the re-crystallization with anhydrous methanol numerous times, the purity of rebaudioside A may be increased to over 95%. U.S. Patent Publication No. 2006/0083838 discloses purification of rebaudioside A through re-crystallization with a solvent comprising ethanol and between 4 and 15% water. Japanese Patent Application No. 55-23756 discloses a method for purifying rebaudioside A and stevioside by crystallization from aqueous ethanol (>70%) to obtain an 80% pure rebaudioside A. U.S. Patent Publication No. 2007/0082103 discloses a method for purifying rebaudioside A by recrystallization from aqueous ethanol, asserting a two-step recrystallization from crude rebaudioside (60%) results in the formation of >98% pure rebaudioside at 97% yield. These prior art methods, however, do not provide a substantially pure rebaudioside A composition using only a single recrystallization step.

Accordingly, there exists a need for a simple, efficient, and economical method for producing substantially pure rebaudioside A.

SUMMARY OF INVENTION

Exemplary embodiments of the invention address the above-identified need by providing a substantially pure rebaudioside A, polymorphic and amorphous forms of rebaudioside A, methods for purifying rebaudioside A, and methods for making polymorphic and amorphous forms of rebaudioside A.

In a particular embodiment, the method for purifying rebaudioside A comprises a simple crystallization. In one embodiment, a method for purifying rebaudioside A comprises combining crude rebaudioside A and an aqueous organic solvent to form a rebaudioside A solution, the aqueous organic solution comprising water in an amount from about 10% to about 25% by weight, and crystallizing from the crude rebaudioside A solution, in a single step, a substantially pure rebaudioside A in a purity greater than about 95% by weight on a dry basis.

In other particular embodiments, different polymorphic and amorphous forms of rebaudioside A and methods for preparing different polymorphic and amorphous forms of rebaudioside A are provided.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION OF INVENTION

Rebaudioside A is a natural high-potency sweetener that generally is available at moderate cost at ≤80% purity and at >80% purity only at high cost. Commercial samples of rebaudioside A often have a bitter taste that is believed to be due to impurities. Accordingly, there exists a need for a substantially pure rebaudioside A and a simple and economic method for purifying rebaudioside A in order to obtain a substantially pure rebaudioside A suitable for use as a natural high-potency sweetener.

As used herein, the term "substantially" or "substantially pure" refers to a rebaudioside A composition that includes at least about 85% by dry weight of the rebaudioside A, in another embodiment at least about 90% by dry weight, in another embodiment from about 95% to about 98% by dry weight, and in yet another embodiment from about 99% to about 100% by dry weight.

Exemplary embodiments of this invention satisfy these needs by providing a method for purifying crude rebaudioside A to substantially pure rebaudioside A by crystallizing a crude rebaudioside A from an aqueous organic solution comprising water in an amount from about 10% to about 25% by weight and crystallizing in at least one step a substantially pure rebaudioside A. Other exemplary embodiments of this invention encompass a composition of a substantially pure rebaudioside A and compositions comprising one, or more than one, polymorph(s) of rebaudioside A. Still other exemplary embodiments of this invention encompass an amorphous form of rebaudioside A and methods of preparing amorphous forms of rebaudioside A. In yet another embodiment, a method for converting one form of polymorph into another form of polymorph or amorphous form is provided. Exemplary embodiments of this invention are described in detail below and illustrated in FIGS. 1-11.

Method of Purifying Crude Rebaudioside A Mixture

Crude rebaudioside A products are commercially available comprising rebaudioside A in purities from about 40% to about 95% by weight, about 60% to about 85% by weight, or about 70% to about 85% by weight. It is envisioned that crude rebaudioside A in its raw form as extracted from *Stevia* plants, may be purified by recrystallization. The primary impurities, identified by HPLC, are stevioside, rebaudioside B, rebaudioside C, and rebaudioside D. Rebaudioside D impurities can be removed by increasing the amount of water in an aqueous organic recrystallization solvent; however, excessive water content in the crystallization solvent will result in a lower recovery of rebaudioside A. Rebaudioside B impurity can be reduced significantly by slurrying the crude rebaudioside A in an organic solvent or an aqueous organic solution or through treatment of the crude rebaudioside A solution with an anion exchange resin. Accordingly, the method of purification depends on the impurities present in the crude rebaudioside A starting material.

Figure 1:
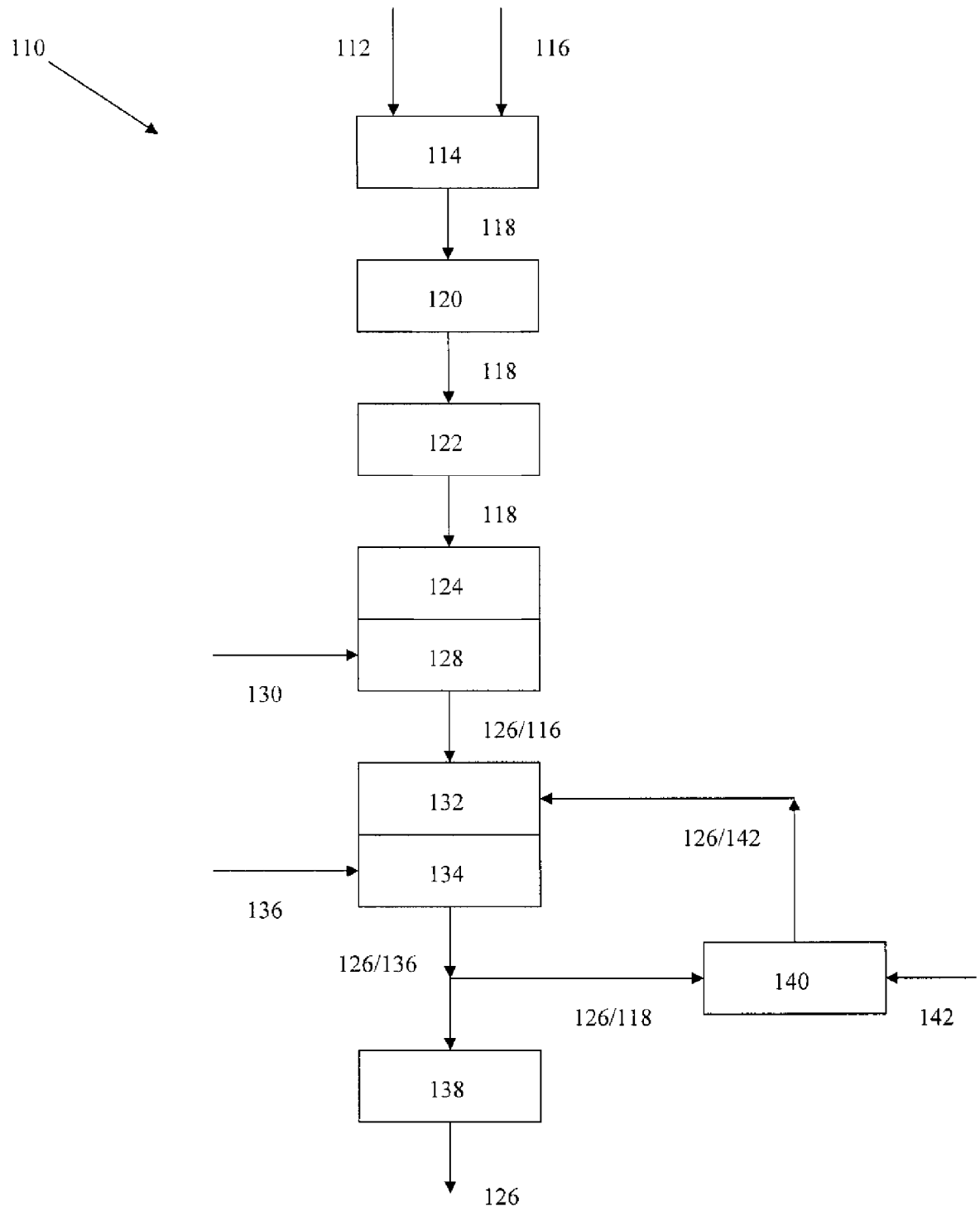
FIG. 1 is a schematic illustrating a method for purifying rebaudioside A in accordance with an embodiment of this invention.

In an exemplary embodiment of a method for purifying rebaudioside A 110, illustrated in FIG. 1, crude rebaudioside A 112 may be combined 114 with an aqueous organic solution 116 to form a rebaudioside A solution 118. The aqueous organic solution 116 comprises water in an amount from about 10% to about 25% by weight and at least one organic solvent. Alternatively, the aqueous organic solution 116 may comprise water in an amount from about 15% to about 20% by weight and at least one organic solvent.

Aqueous organic solvents, as used herein, refer to mixtures of water and at least one organic solvent. Non-limiting examples of organic solvents include alcohol, acetone, and acetonitrile. Alcohol, as used herein, refers to any straight, branched, or cyclic; substituted or unsubstituted alkyl, alkenyl, or alkynyl group attached to at least one hydroxyl moiety. Non-limiting examples of alcohols include ethanol, methanol, isopropanol, 1-propanol, 1-butanol, 2-butanol, tert-butanol, and isobutanol.

In an exemplary embodiment, the aqueous organic solution 116 comprises a mixture of water and at least one organic solvent. In another exemplary embodiment, at least one organic solvent comprises an alcohol, the alcohol comprising ethanol, methanol, or mixtures thereof. In exemplary embodiments wherein the at least one organic solvent comprises a mixture of ethanol and methanol, the ethanol and methanol may be combined in the aqueous organic solvent in a weight ratio ranging from about 20 parts to about 1 part ethanol to about 1 part methanol. In another exemplary embodiment, the ethanol and methanol may be combined in the aqueous organic solvent in a weight ratio ranging from about 3 parts to about 1 part ethanol to about 1 part methanol.

In an exemplary embodiment the rebaudioside A solution 118 comprises the aqueous organic solvent 116 and the crude rebaudioside A 112 in a weight ratio ranging from about 10 to about 4 parts aqueous organic solvent to about 1 part crude rebaudioside A. In another exemplary embodiment, the rebaudioside A solution 118 comprises the aqueous organic solution 116 and the crude rebaudioside A 112 in a weight ratio ranging from about 5 to about 3 parts aqueous organic solvent to about 1 part crude rebaudioside A.

In an exemplary embodiment, the method 110 may be carried out at approximately room temperature. In another embodiment, the method 110 further comprises the step of heating 120 the rebaudioside A solution 118. In an embodiment, the step of heating 120 the rebaudioside A solution 118 comprises heating the rebaudioside A solution to a temperature in a range from about 20° C. to about 70° C., from about 20° C. to about 60° C., from about 20° C. to about 40° C., or from about 40° C. to about 60° C. In another embodiment, the step of heating 120 the rebaudioside A solution 118 comprises heating the rebaudioside A solution to about reflux temperature. The step of heating 120 the rebaudioside A solution 118 comprises heating the rebaudioside A solution for about 0.25 hours to about 8 hours. In another exemplary embodiment, wherein the method for purifying rebaudioside A 110 comprises the step of heating 120 the rebaudioside A solution 118, the method further comprises the step of cooling 122 the rebaudioside A solution. In an embodiment, the step of cooling 122 the rebaudioside A solution 118 comprises cooling the rebaudioside A solution to a temperature in the range from about 4° C. to about 25° C. The step of cooling 122 the rebaudioside A solution 118 comprises cooling the rebaudioside A solution for about 0.5 hours to about 24 hours.

The method for purifying rebaudioside A 110 further comprises the step of crystallizing 124 from the rebaudioside A solution 118 in a single step a substantially pure rebaudioside A composition 126 comprising rebaudioside A in an amount greater than about 85% by weight on a dry basis, greater than about 90% by weight on a dry basis, greater than about 95% by weight on a dry basis, greater than about 97% by weight on a dry basis, greater than about 98% by weight on a dry basis, or greater than about 99% by weight on a dry basis. The rebaudioside A solution 118 during the single crystallization step may be stirred or unstirred.

In an exemplary embodiment, the method 110 may further comprise the optional step of seeding 128 the rebaudioside A solution 118 at an appropriate temperature with substantially pure crystals of rebaudioside A 130 sufficient to promote crystallization of the rebaudioside A to form pure rebaudioside A. An amount of rebaudioside A 130 sufficient to promote crystallization of substantially pure rebaudioside A 126 comprises an amount of rebaudioside A from about 0.0001% to about 1% by weight of the rebaudioside A present in the solution. In another embodiment, an amount of rebaudioside A 130 sufficient to promote crystallization of the rebaudioside A to form a composition of a substantially pure rebaudioside A 126 comprises an amount of rebaudioside A from about 0.01% to about 1% by weight. An appropriate temperature for the step of seeding 128 comprises a temperature in a range from about 18° C. to about 35° C.

In another exemplary embodiment, the method further comprises the steps of separating 132 and washing 134 the substantially pure rebaudioside A composition 126. The substantially pure rebaudioside A composition 126 may be separated from the aqueous organic solution 118 by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any pressure, vacuum, or gravity filtration methods, that include without limitation, the use of belt, drum, nutsche type, leaf, plate, Rosenmund type, sparkler type, and bag filters and filter press. Operation of the rebaudioside A solid-liquid separation device may be continuous, semi-continuous or in batch mode. The substantially pure rebaudioside A composition 126 also may be washed 134 on the separation device using various aqueous organic solvents 136 and mixtures thereof. The substantially pure rebaudioside A composition 126 can be partially or totally dried on the separation device using any number of gases, including, without limitation, nitrogen or argon, to evaporate residual liquid solvent 136. The substantially pure rebaudioside A composition 126 may be automatically or manually removed from the separation device using liquids, gases or mechanical means by either dissolving the solid or maintaining the solid form.

In still another exemplary embodiment, the method 110 further comprises the step of drying 138 the substantially pure rebaudioside A composition 126. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the step of drying 138 comprises drying the substantially pure rebaudioside A composition 126 using a nitrogen or argon purge to remove the residual solvent 120 at a temperature in a range from about 40° C. to about 60° C. for about 5 hours to about 100 hours.

In yet another exemplary embodiment, wherein the crude rebaudioside A mixture 112 comprises substantially no rebaudioside D impurity, the method 110 further comprises the step of slurrying 140 the composition of substantially pure rebaudioside A 126 with an organic solvent or an aqueous organic solvent 142 prior to the step of drying 138 the substantially pure rebaudioside A composition. The slurry may be a mixture comprising a solid and an aqueous organic solvent or organic solvent, wherein the solid comprises the substantially pure rebaudioside A composition 126 and is only sparingly soluble in the aqueous organic solvent or organic solvent 142. In an embodiment, the substantially pure rebaudioside A composition 126 and aqueous organic solvent or organic solvent 142 may be present in the slurry in a weight ratio ranging from about 15 parts to about 1 part aqueous organic solvent to about 1 part substantially pure rebaudioside A composition. In one embodiment, the slurry may be maintained at room temperature. In another embodiment, the step of slurrying 140 comprises heating the slurry to a temperature in a range from about 20° C. to about 40° C. The substantially pure rebaudioside A composition 126 may be slurried for about 0.5 hours to about 24 hours.

In still yet another exemplary embodiment, the method further comprises the steps of separating 132 the substantially pure rebaudioside A composition 126 from the aqueous organic solvent 142 of the slurry and washing 134 the substantially pure rebaudioside A composition followed by the step of drying 138 the substantially pure rebaudioside A composition.

If further purification is desired, the method of purifying rebaudioside A 110 described herein may be repeated or the substantially pure rebaudioside A composition may be further purified using an alternative purification method, such as the column chromatography.

Purity, as used herein, represents the weight percentage of rebaudioside A present in a rebaudioside A composition in raw or purified form. In one embodiment, a rebaudioside A composition comprises rebaudioside A in a particular purity, with the remainder of the composition comprising a mixture of other steviol glycosides or any component that is not rebaudioside A. The purity of the composition may be measured using methods known to those of ordinary skill in the art. One such method includes high performance liquid chromatography (HPLC). Those of ordinary skill in the art also should appreciate that the moisture in the sample may affect the accuracy of purity measurements. Accordingly, the composition should be substantially dry when measured for purity. As used herein, a substantially dry composition comprises up to about 10% by weight of moisture.

Rebaudioside A Polymorphic and Amorphous Forms

The purification of rebaudioside A using the method described hereinabove results in the formation of at least three different polymorphs of rebaudioside A: Form 1: a rebaudioside A hydrate; Form 2: an anhydrous rebaudioside A, and Form 3: a rebaudioside A solvate. Those of ordinary skill in the art will appreciate that both the aqueous organic solution and the temperatures of the purification process described herein may influence the resulting polymorphs of a substantially pure rebaudioside A composition.

Polymorphism is defined as the ability of a substance to exist as two or more crystalline states that have different arrangements and/or conformations of the molecules in the crystal lattice. Approximately 30% of organic compounds are believed to exhibit polymorphism (Zell, et al., *Tetrahedron* 56(36)6603-16 (2000)). Polymorphism is important in the formulation of pharmaceuticals, pigments and dyes, sweeteners, explosives, and agrochemicals. Polymorphism may cause physical properties such as density, melting point, and rate of dissolution to change.

The polymorphs of rebaudioside A were identified by analysis of samples with powder x-ray diffraction (XRPD), a technique well known to those skilled in the art. FIGS. 3-11 are XRPD scans of substantially pure rebaudioside A compositions obtained from the purification process described herein. The XRPD scans of rebaudioside A polymorphs were created by plotting the scattering intensity versus the scattering angle 2θ. Samples were analyzed by XRPD using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1°, and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment. Data were collected and analyzed using XRD-60000 v. 4.1. The patterns exhibit resolution of reflections, indicating that the samples are comprised of crystalline material.

Figure 3:
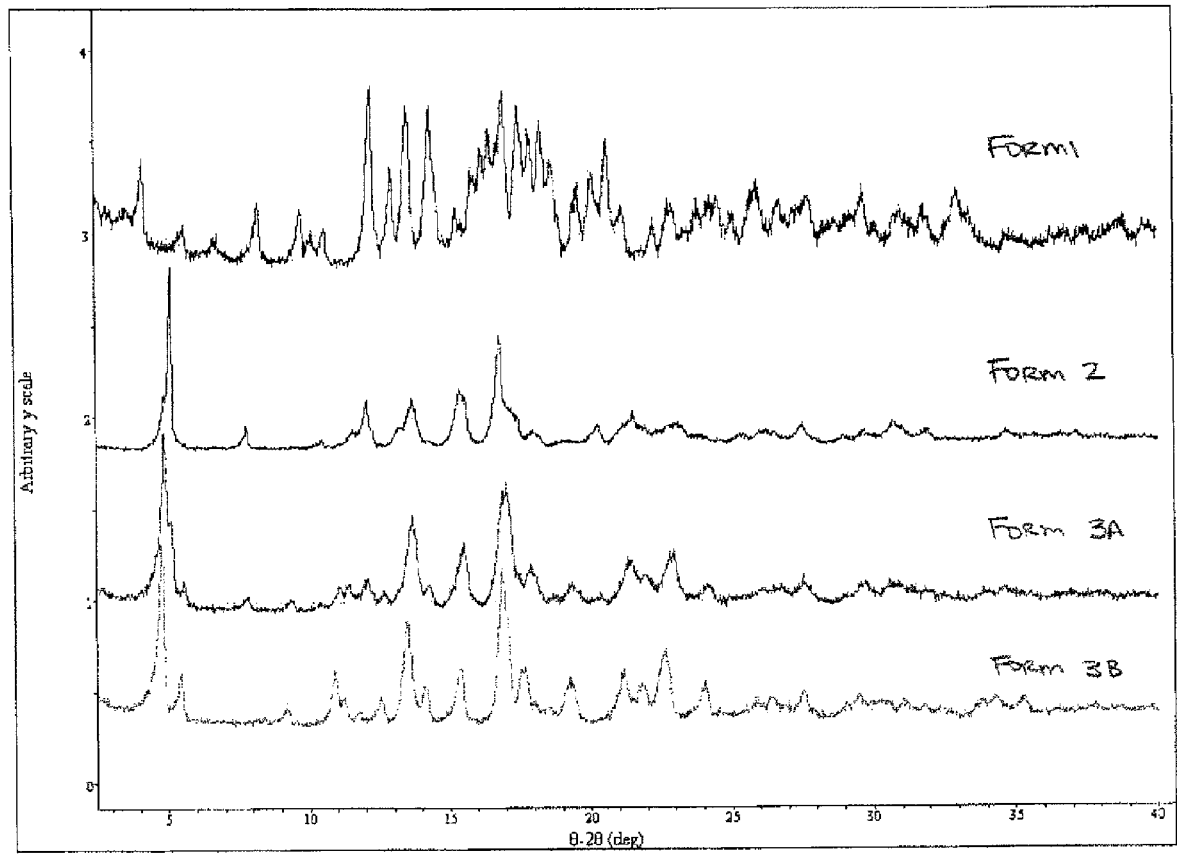
FIG. 3 is a powder x-ray diffraction scan comparing four rebaudioside A polymorphs, Forms 1, 2, 3A and 3B, on a plot of the scattering intensity versus the scattering angle 2θ in accordance with an embodiment of this invention.

FIG. 3 shows representative patterns for Form 1, Form 2, and Forms 3A (methanol solvate) and 3B (ethanol solvate). The pattern for Form 2 (top pattern) is distinctively different from the other patterns. It should be noted that multiple polymorphs can exist within each classification of Forms 1, 2, and 3.

Figure 4:
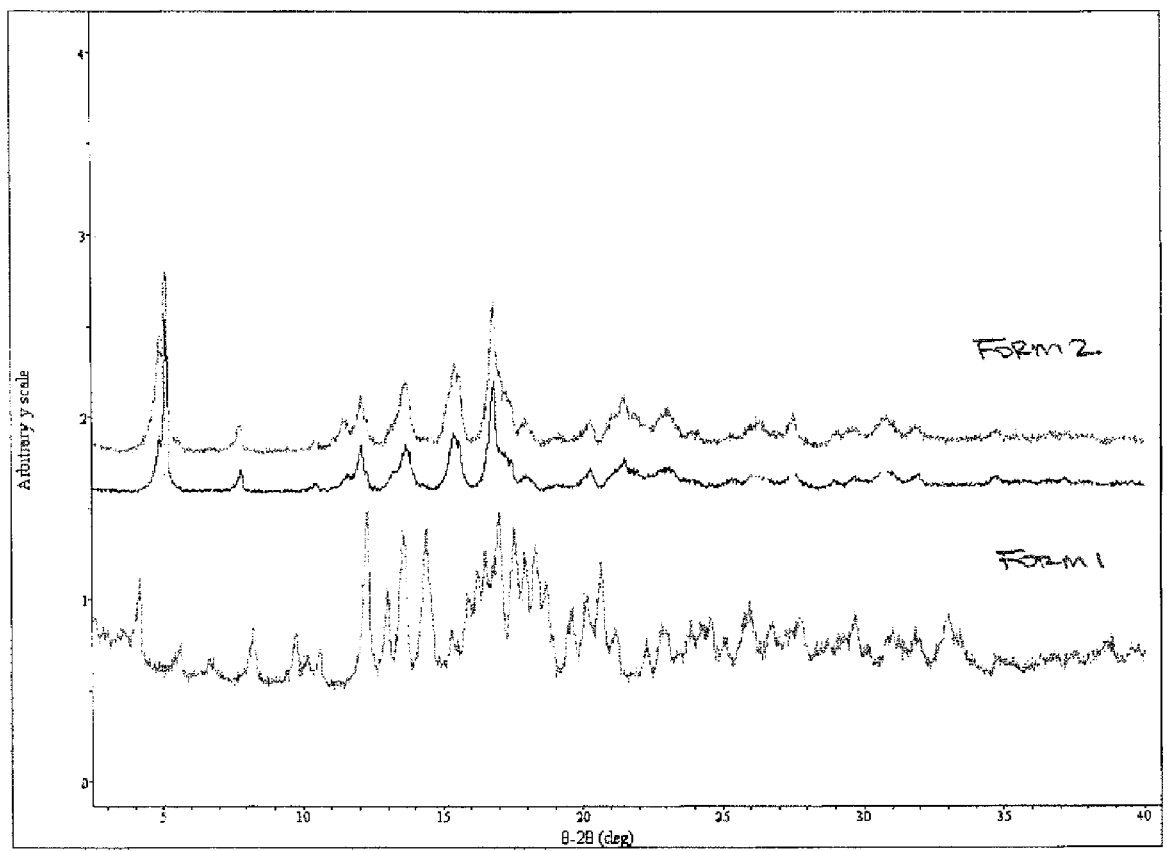
FIG. 4 is a powder x-ray diffraction scan comparing rebaudioside A polymorphs, Form 1 and Form 2, on a plot of the scattering intensity versus the scattering angle 2θ in accordance with an embodiment of this invention.

FIG. 4 highlights the differences between Forms 1 and 2. Additionally, the two patterns of Form 2 are shown to illustrate the reproducibility in generation of the different polymorphs under varying recrystallization conditions of the polymorphs.

Figure 5:
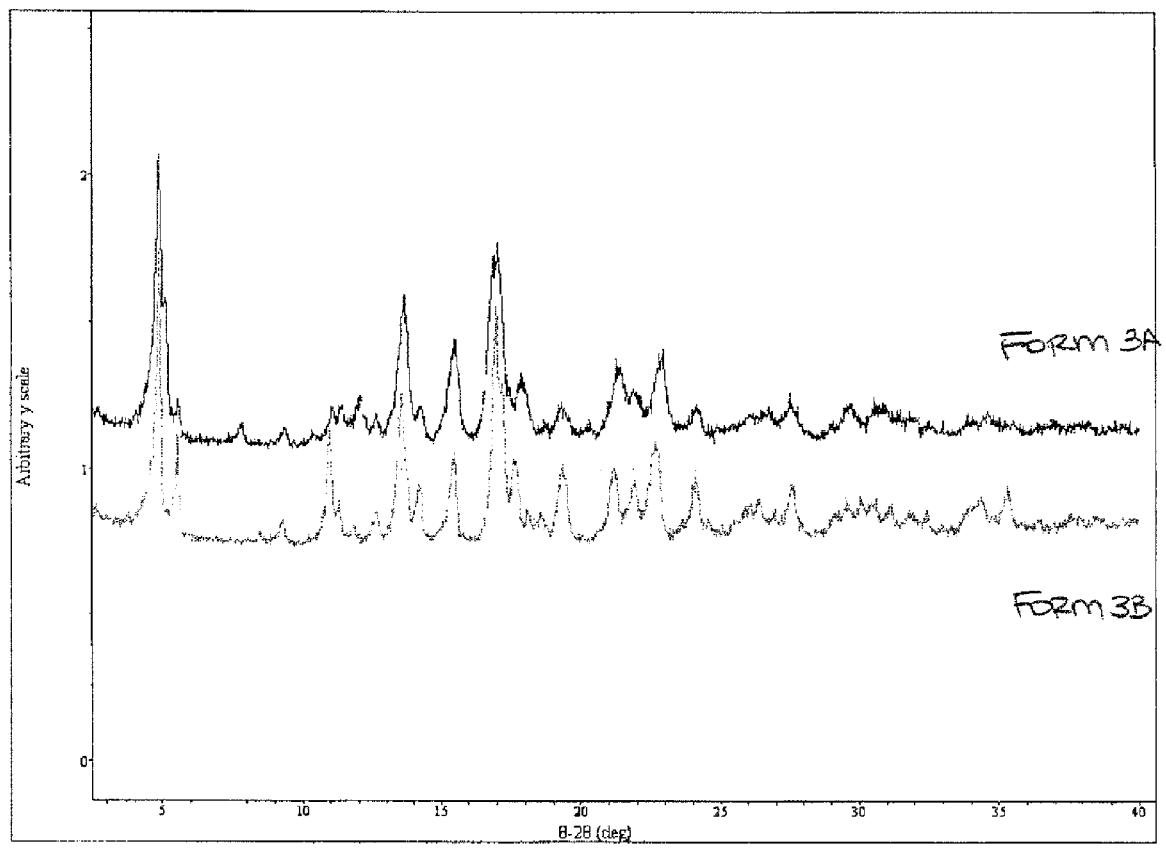
FIG. 5 is a powder x-ray diffraction scan comparing rebaudioside A polymorphs, Form 3A and Form 3B, on a plot of the scattering intensity versus the scattering angle 2θ in accordance with an embodiment of this invention.

FIG. 5 shows a significant similarity between the XRPD patterns of Forms 3A and 3B. Not wishing to be bound by any theory, it is possible that these polymorphs are isostructural solvates, wherein the only differences between the patterns are the shifting of certain peaks due to the variation of the solvent identity. This isostructural relationship between Forms 3A and 3B could be verified by indexing the patterns if necessary. The asterisks identify the peaks that are shifted to the right by about 0.2 degrees 2θ in the pattern for Form 3A. In addition, several peaks in Form 3B are more intense than the corresponding peaks in Form 3A. For example, the peaks at 5.5, 11.0, 14.2, and 19.4 degrees are more intense for Form 3B than for Form 3A.

Figure 6:
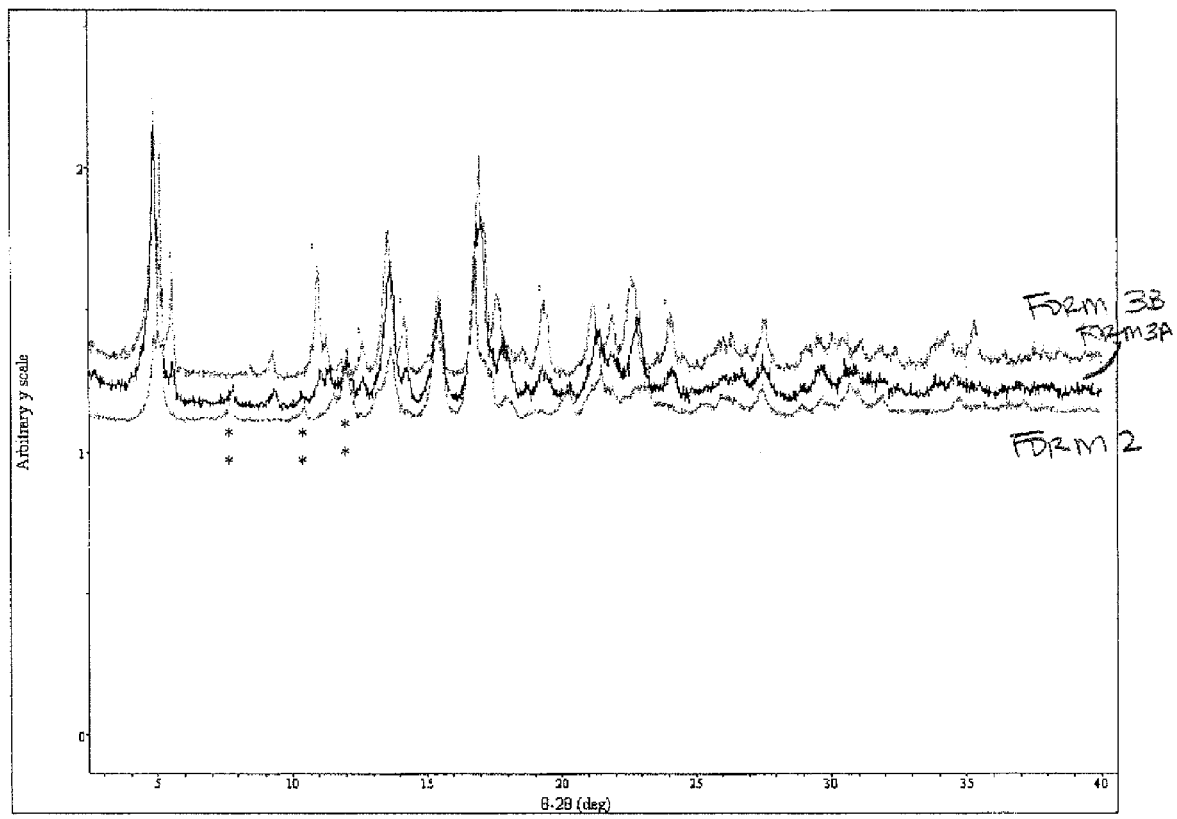
FIG. 6 is a powder x-ray diffraction scan comparing rebaudioside A polymorphs, Forms 2, 3A and 3B, on a plot of the scattering intensity versus the scattering angle 2θ in accordance with an embodiment of this invention.
Figure 7:
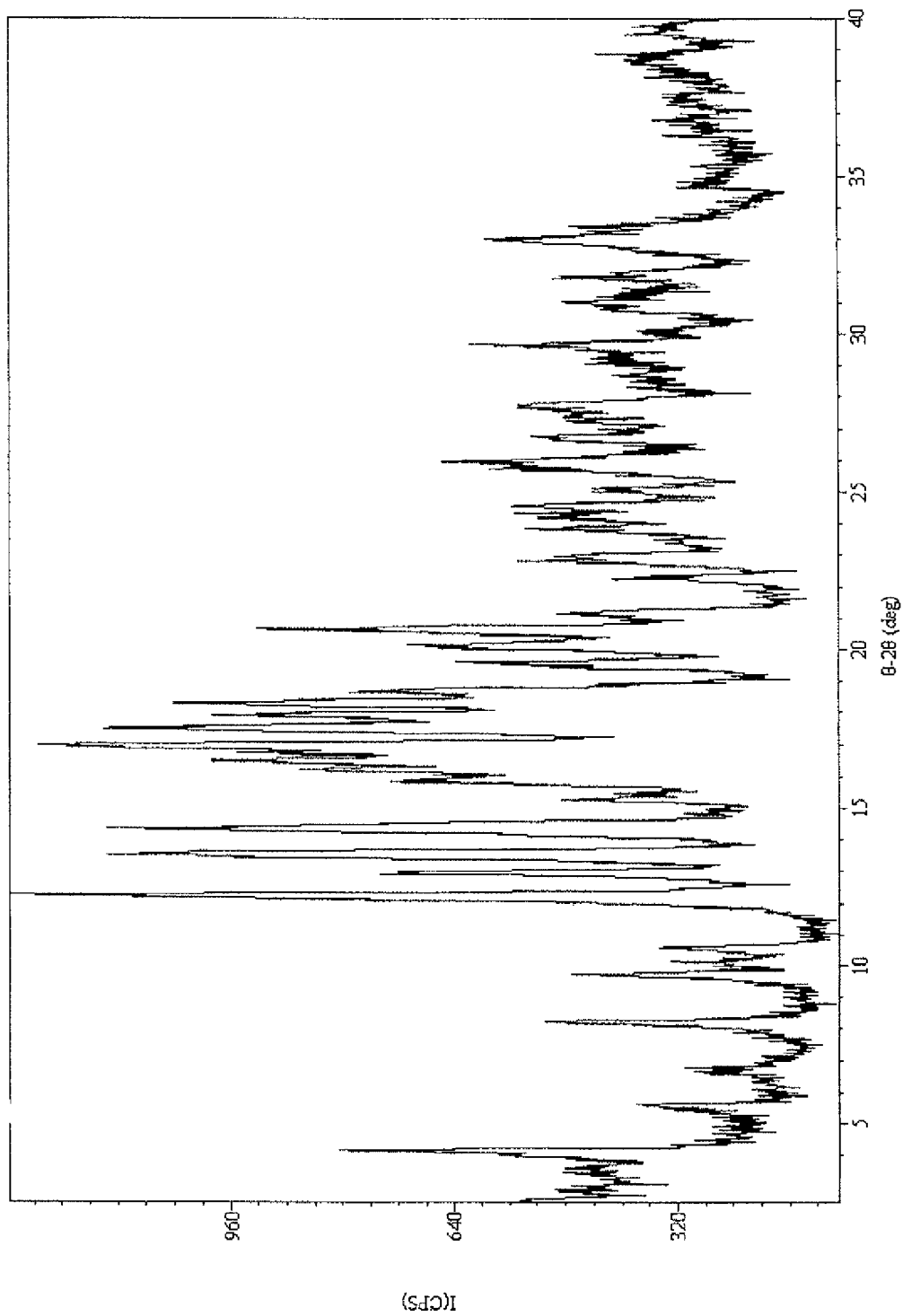
FIG. 7 is a powder x-ray diffraction scan of rebaudioside A polymorph Form 1 on a plot of the scattering intensity versus the scattering angle 2θ in accordance with an embodiment of this invention.
Figure 8:
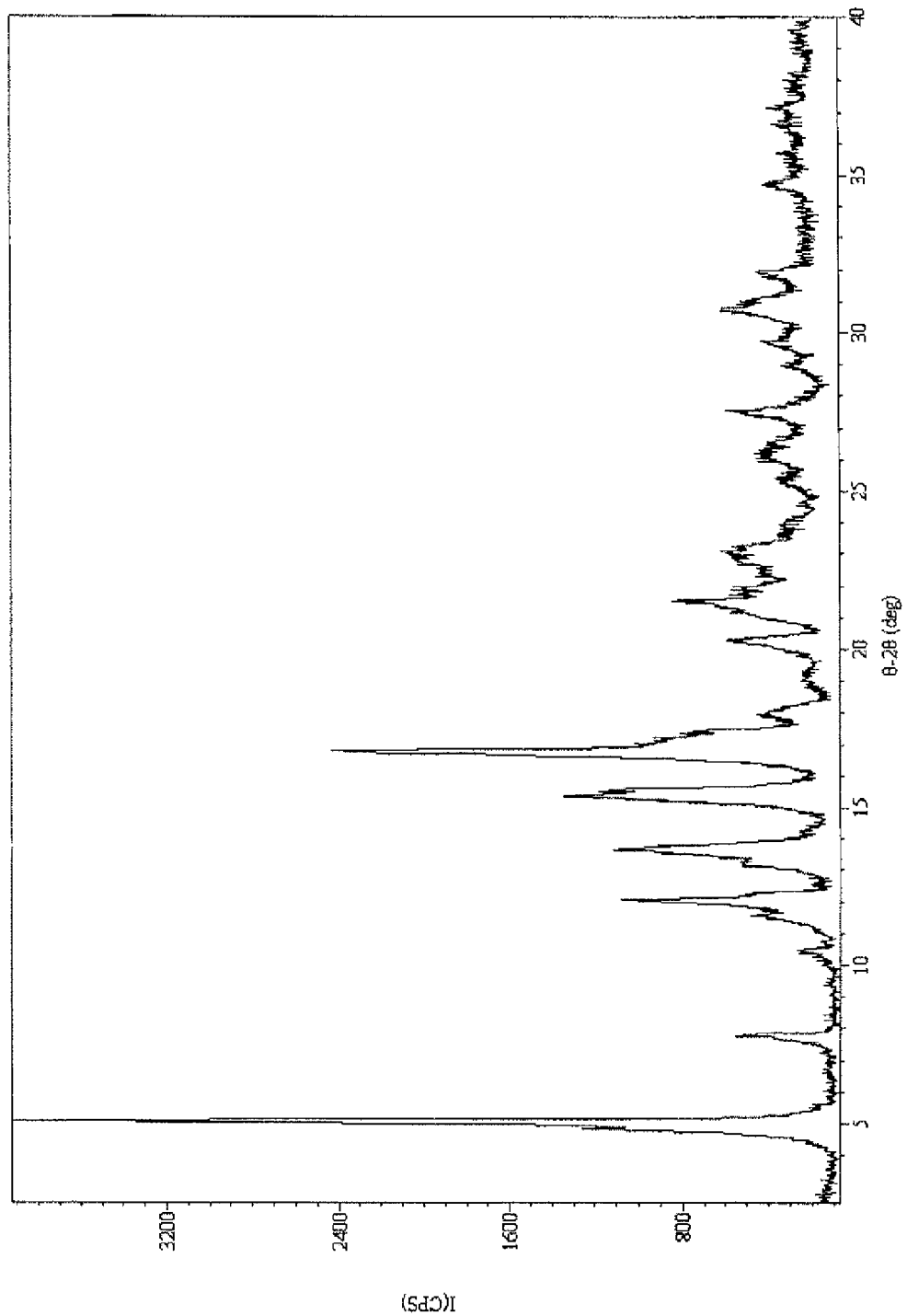
FIG. 8 is a powder x-ray diffraction scan of rebaudioside A polymorph Form 2 on a plot of the scattering intensity versus the scattering angle 2θ in accordance with an embodiment of this invention.
Figure 9:
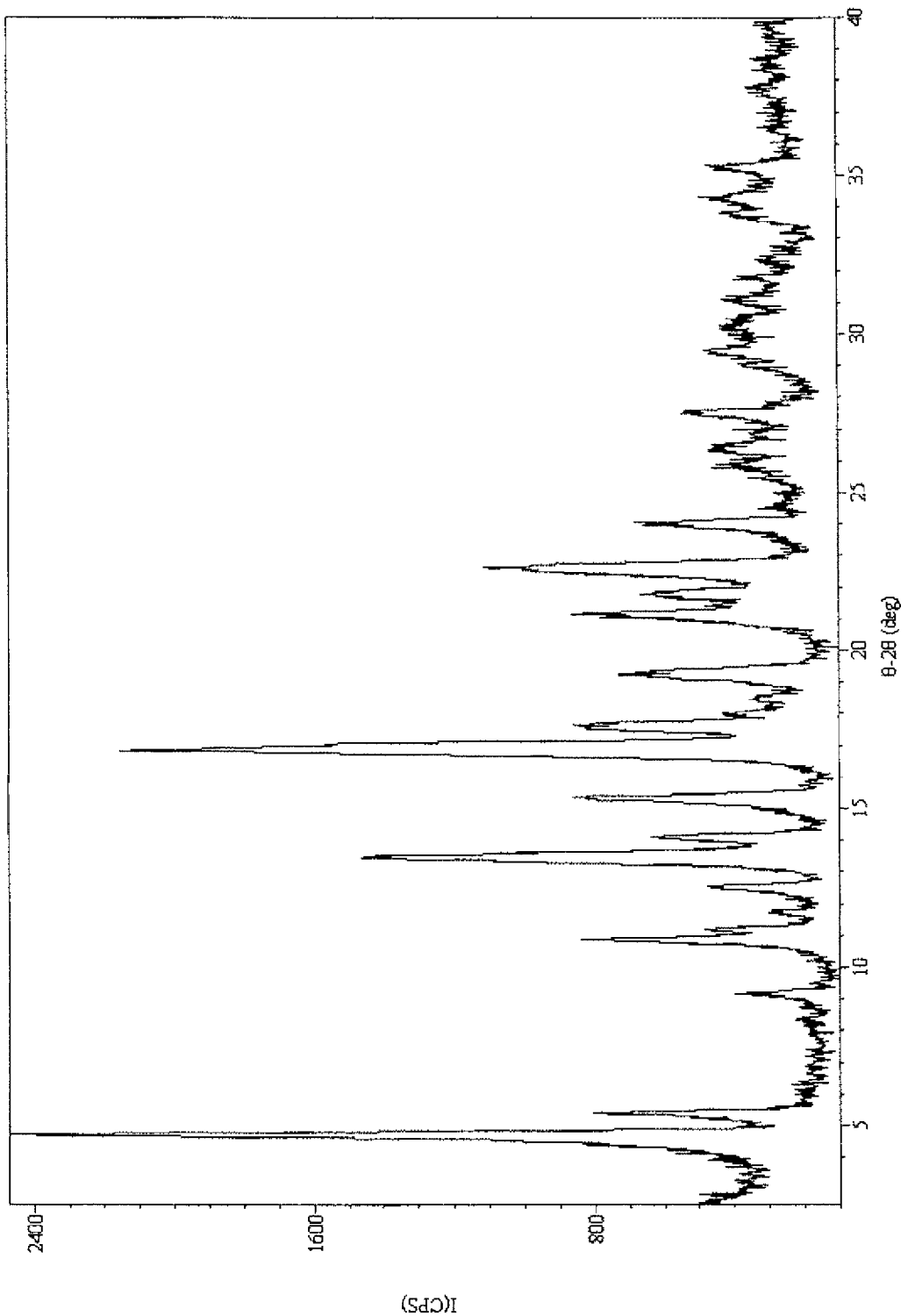
FIG. 9 is a powder x-ray diffraction scan of rebaudioside A polymorph Form 3A on a plot of the scattering intensity versus the scattering angle 2θ in accordance with an embodiment of this invention.
Figure 10:
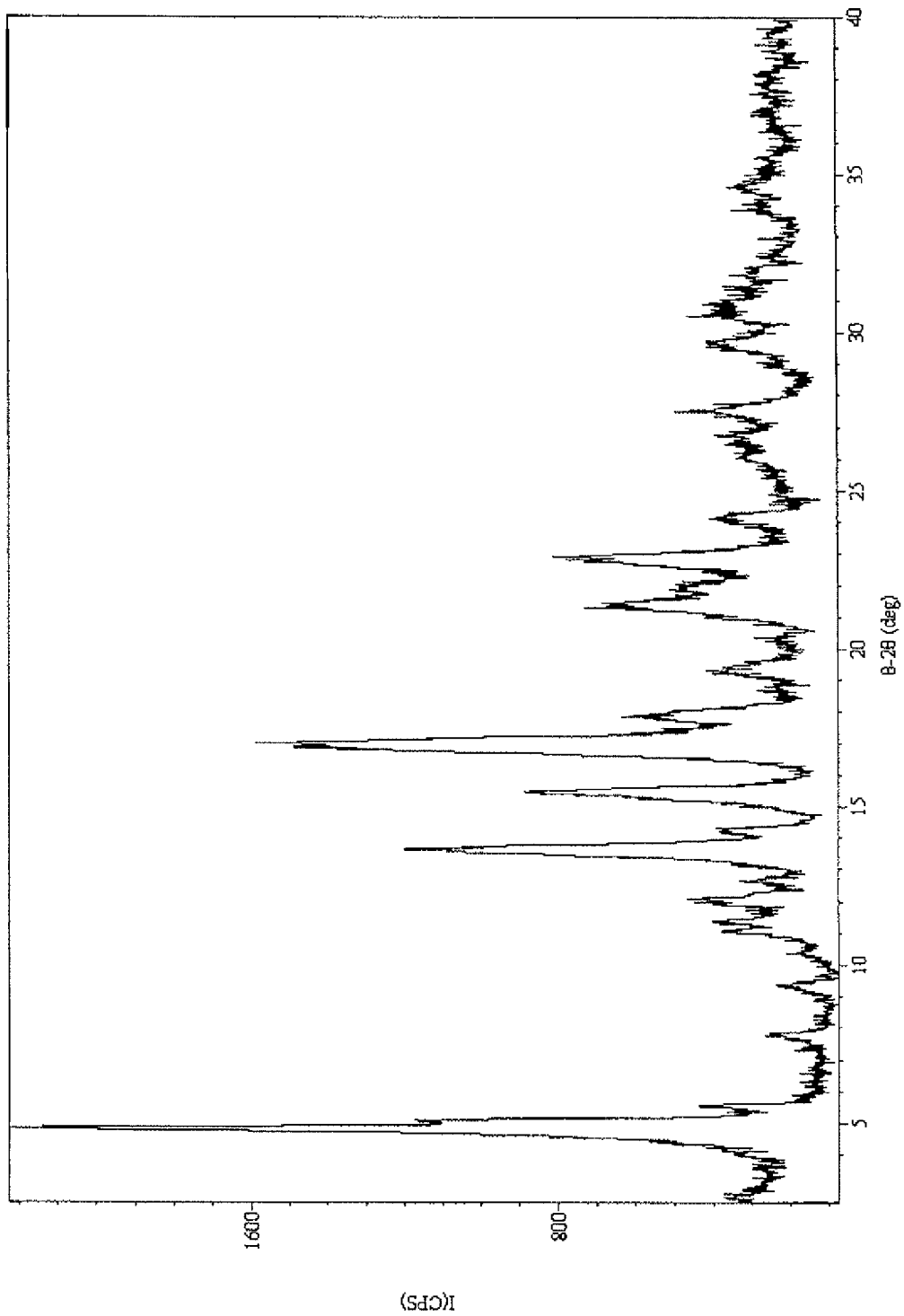
FIG. 10 is a powder x-ray diffraction scan of rebaudioside A polymorph Form 3B on a plot of the scattering intensity versus the scattering angle 2θ in accordance with an embodiment of this invention.

FIG. 6 compares Form 2 to Forms 3A and 3B from FIG. 5. Form 2 is more similar to Form 3A than to that of Form 3B. Although the peaks identified in FIG. 5 as being more intense in Form 3B than in Form 3A are not observed in the pattern of Form 2, there are at least three peaks (marked with a double-asterisks underneath the patterns) that show the reverse trend (i.e., the peaks are present in Form 2, small in Form 3A, and larger in Form 3B). Finally, a large peak in Form 3B at 17.6 degrees appears to be shifted slightly to the right in Form 3A (17.9 degrees) and shifted further to the right in Form 2 (18.0 degrees). Two other sets of peaks between 21 and 23 degrees show this shifting as well. Not wishing to be bound by any theory, the shifting of the peaks may be an indication that Form 3A is partially desolvated, thus containing a mixture of both the solvate and Form 2 crystals.

FIGS. 7-10 are XRPD scans of the individual polymorphs Form 1, Form 2, Form 3A, and Form 3B, respectively, from a substantially pure rebaudioside A composition obtained from the purification process described hereinabove.

Figure 2:
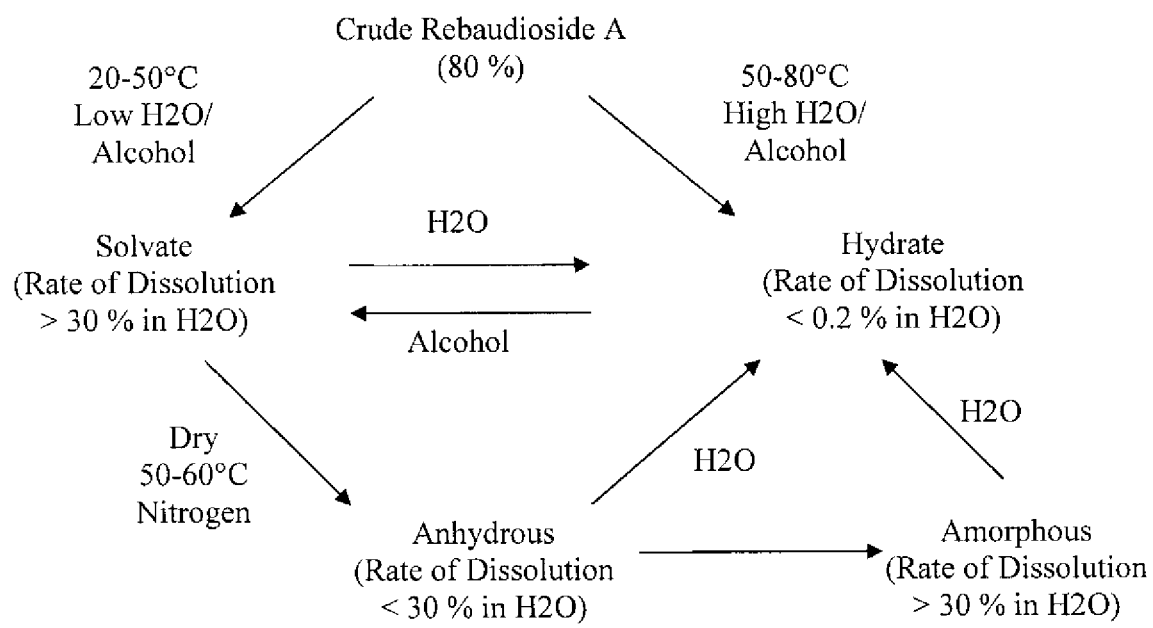
FIG. 2 is a schematic of the formation and conversion of rebaudioside A polymorphic and amorphous forms of rebaudioside A in accordance with an embodiment of this invention.

As illustrated in FIG. 2, the type of polymorph formed may be dependent on the factors such as the composition of the aqueous organic solution, the temperature of the crystallization step, and the temperature during the drying step. Not wishing to be bound by any theory, Form 1 and Form 3 are believed to be formed during the single crystallization step while Form 2 is believed to be formed during the drying step after conversion from Form 1 and Form 3.

Low temperatures during the crystallization step, in the range of about 20° C. to about 50° C., and a low ratio of water to the organic solvent in the aqueous organic solvent results in the formation of Form 3. High temperatures during the crystallization step, in the range of about 50° C. to about 80° C., and a high ratio of water to the organic solvent in the aqueous organic solvent results in the formation of the Form 1. Form 1 can be converted to Form 3 by slurrying in an anhydrous solvent at about room temperature for about 2 to about 16 hours or by slurrying in an anhydrous solvent at about reflux temperature for about 0.5 to about 3 hours. Form 3 can be converted to Form 1 by slurrying the polymorph in water at about room temperature for approximately 16 hours or at about reflux temperature for about 2 to about 3 hours. Form 3 can be converted to the Form 2 during the drying process; however, increasing either the drying temperature above about 70° C. or the drying time of a substantially pure rebaudioside A composition can result in decomposition of the rebaudioside A and increase the remaining rebaudioside B impurity in the substantially pure rebaudioside A composition. Form 2 can be converted to Form 1 with the addition of water.

Figure 11:
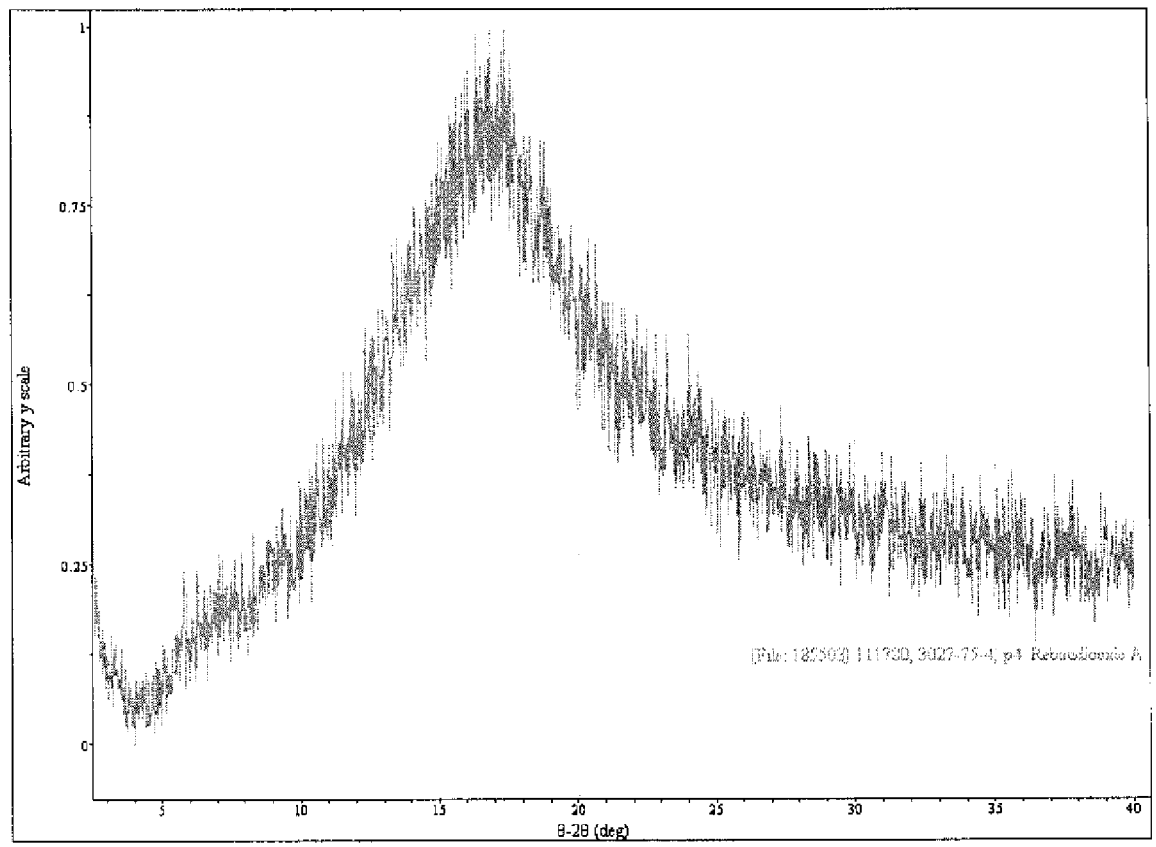
FIG. 11 is a powder x-ray diffraction scan of rebaudioside A amorphous Form 4 on a plot of the scattering intensity versus the scattering angle 2θ in accordance with an embodiment of this invention.

In addition to the at least three polymorphic forms of rebaudioside A, the purification of rebaudioside A may result in the formation of an amorphous form of rebaudioside A, Form 4, as shown in FIG. 11. Form 4 has a broad amorphous halo that identifies the composition as being amorphous.

Amorphous, as used herein, describes a non-crystalline solid material. The amorphous form of rebaudioside A (Form 4) has an improved rate of dissolution as compared to the polymorphic forms of rebaudioside A (Forms 1, 2, or 3). Those of ordinary skill in the art should appreciate that the rate of dissolution of a sweetener composition may be important in the formulation of solid and liquid sweetenable compositions, non-limiting examples of which include chewing gum, baked goods, and beverages.

As described hereinabove, Form 4 may be obtained during the initial purification of rebaudioside A or directly from any individual polymorph or combination of polymorphs using methods well known to those of ordinary skill in the art. In addition, Form 4 may be obtained from a crude rebaudioside A composition or a substantially pure rebaudioside A composition obtained through purification means other than those described hereinabove. Non-limiting examples of methods for preparing amorphous forms of rebaudioside A include ball milling, precipitation, lyophilization, cryogrinding, and spray-drying of a rebaudioside A composition.

In a particular embodiment, the purification of rebaudioside A described hereinabove results in a composition comprising the amorphous rebaudioside A of Form 4. Those of ordinary skill in the art should appreciate that the parameters of the crystallization procedure may be modified to enhance the formation of Form 4.

In another particular embodiment, Form 4 can be prepared from a rebaudioside A composition by spray-drying a solution of the rebaudioside A composition. Briefly described, spray-drying generally requires the feed of a solution of rebaudioside A through a feed pump into a nozzle atomizer which atomizes the solution into a spray of droplets with the help of a constant flow of nitrogen/air. The moisture is evaporated from the droplets under controlled temperature conditions and airflow conditions in the drying chamber, resulting in the formation of dry particles of amorphous rebaudioside A. The purity of the amorphous rebaudioside A will depend upon the purity of the solution of rebaudioside A.

In another particular embodiment, Form 4 can be prepared from a rebaudioside A composition by milling non-amorphous forms of rebaudioside A. Milling is a mechanical process that is believed to produce localized areas of energy that convert crystalline forms of rebaudioside A to the amorphous form. Exemplary milling techniques include ball milling or air jet milling, both techniques well known to those of ordinary skill in the art. Briefly described, non-amorphous forms of rebaudioside A are milled for a period of time and at a speed effective to form an amorphous rebaudioside A. These parameters may be determined by those of ordinary skill in the art. Typical milling time periods may range from about 15 minutes to about 2 hours, although other time periods also may be employed.

The material properties of the three rebaudioside A polymorphs and the rebaudioside A amorphous form are summarized in the following table:

TABLE 1

Rebaudioside A Polymorph and Amorphous Forms

|  | Form 1 Polymorph | Form 2 Polymorph | Form 3 Polymorph | Form 4 Amorphous |
|---|---|---|---|---|
| Rate of dissolution in H2O at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 13% | <0.05% |
| Moisture content | >5% | <1% | <3% | <6% |

The above-described material properties are only illustrative of particular embodiments of the polymorphic and amorphous forms of rebaudioside A. Those of ordinary skill in the art should appreciate that the anhydrous rebaudioside A polymorph (Form 2), rebaudioside A solvate polymorph, and amorphous rebaudioside A are hygroscopic and may absorb moisture to an amount up to about 10% by weight on a dry basis.

Those of ordinary skill in the art should appreciate that the rebaudioside A composition may be modified to obtain a desired mixture of rebaudioside A polymorphic and amorphous forms depending on the desired qualities of the rebaudioside A composition (i.e., rate of dissolution, etc.). In one embodiment, a substantially pure rebaudioside A composition may comprise a particular polymorphic or amorphous form of rebaudioside A in an amount in the range of about 1% to about 100% by weight. For example, a substantially pure rebaudioside A composition may comprise a polymorphic or amorphous form of rebaudioside A in an amount greater than about 25% by weight, more particularly in an amount greater than about 50% by weight, still more particularly in an amount greater than about 75% by weight, or still even more particularly in an amount greater than about 85% by weight. Suitable amounts of rebaudioside A polymorphic or amorphous forms also may be used within these ranges. In another embodiment, a substantially pure rebaudioside A composition may comprise a combination of particular polymorphic and/or amorphous form of rebaudioside A.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, percentages (% s) are by weight.

EXAMPLES

The purity of the rebaudioside A compositions described in the examples hereinbelow was determined using HPLC. Methods of performing HPLC analysis are well known to those of ordinary skill in the art. Briefly described, the HPLC analysis was performed using a ZORBAX $NH_2$ column (150× 4.6 mm, 5 µm) at a temperature of 30° C. The mobile phase comprised a solution of 20% buffer (0.0125% acetic acid and 0.0125% ammonium acetate) and 80% acetonitrile at a flow rate of 1.5 mL/min. 12 µL of each sample was injected in duplicate and the sample was analyzed using a UV detector at 210 nm (4 nm bandwidth) with a reference of 260 nm (100 nm bandwidth). The HPLC analysis required a run time ranging from 40 to 60 min.

A buffer solution of 0.0125% acetic acid and 0.0125% ammonium acetate was prepared by dissolving 0.125 g ammonium acetate and 125 μL glacial acetic acid in one liter of water. The retention time of rebaudioside B was adjusted by varying the ratio of ammonium acetate to acetic acid while maintaining a total of 0.025% of both combined. Increasing the amount of acetic acid decreased the retention time of rebaudioside B.

The mobile phase was prepared by mixing the buffer solution with acetonitrile to achieve a rebaudioside A retention time of 7.0±0.5 min. Initially, this was approximately 20% buffer (200 mL of buffer and 800 mL of acetonitrile). Increasing the amount of acetonitrile by 1 to 2% increased the retention time of rebaudioside A by about one minute.

A diluent solution was prepared by mixing 750 mL of acetonitrile and 250 mL of the buffer solution. Rebaudioside A standards were prepared by diluting 20.0±0.5 mg (recorded to the nearest 0.1 mg) of the rebaudioside A standard with 4 mL of the diluent solution to make a standard solution of approximately 5000 mg/L. The rebaudioside A standard solution was injected at 10.8, 11.4, 12.6 and 13.2 μL. The moisture content was measured by Karl Fischer analysis every time a standard was prepared and corrections were made based on the solvent purity according to the certificate of analysis. Alternatively, rebaudioside A standards were prepared by diluting individual samples of 18, 19, 21 and 22 (each ±0.2) mg of rebaudioside A standard with 4 mL of the diluent solution (correcting for moisture and purity). The individually prepared samples were injected at the same level as the samples (12 μL).

Stevioside standards were prepared by diluting 12.5±0.5 mg (recorded to the nearest 0.1 mg) of the stevioside standard with 5 mL of the diluent solution to make a standard solution of approximately 2500 mg/L standard (stock A) (correcting for moisture and purity). The stevioside standard was then diluted using one mL of stock A to ten mL of diluent to produce a 250 mg/L standard (stock B), and stock standards were diluted to final concentrations ranging from 2.5 to 50 mg/L.

Samples of the rebaudioside A compositions were prepared by diluting 125±2 mg (recorded to the nearest 0.1 mg) of the rebaudioside A composition with 25 mL of the diluent solution to make a sample solution of approximately 5000 mg/L (correcting for moisture). If the samples were not analyzed immediately, they were stored without headspace, under nitrogen, and desiccated.

The following table provides a guideline for retention times (RT) for rebaudioside A and other steviol glycosides. However, those of ordinary skill in the art should appreciate that the retention times may be modified as needed.

TABLE 2

HPLC Retention Guidelines

| Compound | RT (min) |
| --- | --- |
| Stevioside | 4.53 |
| Rebaudioside C | 5.21 |
| Rebaudioside F | 5.62 |
| Rebaudioside A | 7.07 |
| Rebaudioside D | 15.79 |
| Steviolbioside | 18.35 |
| Rebaudioside B | 35.83 |

Example Set A

TABLE 3

Summary of Examples A1-3

| | Crude Rebaudioside A (g) | Ethanol (95%)(mL) | Solvent Methanol (99%)(mL) | Water (mL) | Heating T (° C.) | Drying T (° C.) | Yield (g) | HPLC Purity (wt/wt %) |
| --- | --- | --- | --- | --- | --- | --- | --- | --- |
| A1 | 400 | 1200 | 400 | 320 | 50 | 50 | 130 | 98.9 |
| A2 | 100 | 320 | 120 | 50 | 30-40 | 60 | 72 | 98.3 |
| A3 | 50 | 160 | 60 | 25 | ~30 | 60 | 27.3 | 98.2 |

Example A1

Crude rebaudioside A (77.4% purity) mixture was obtained from a commercial source. The impurities (6.2% stevioside, 5.6% rebaudioside C, 0.6% rebaudioside F, 1.0% other steviol glycosides, 3.0% rebaudioside D, 4.9% rebaudioside B, 0.3% steviolbioside) were identified and quantified using HPLC on a dry basis (moisture content 4.7%).

Crude rebaudioside A (400 g), ethanol (95%, 1200 mL), methanol (99% 400 mL) and water (320 mL) were combined and heated to 50° C. for 10 minutes. The clear solution was cooled to 22° C. for 16 hours. The white crystals were filtered and washed twice with ethanol (2×200 mL, 95%) and dried in a vacuum oven at 50° C. for 16-24 hours under reduced pressure (20 mm).

The final composition of substantially pure rebaudioside A (130 g) comprised 98.91% rebaudioside A, 0.06% stevioside, 0.03% rebaudioside C, 0.12% rebaudioside F, 0.13% other steviol glycosides, 0.1% rebaudioside D, 0.49% rebaudioside B and 0.03% steviolbioside, all by weight.

Example A2

Crude rebaudioside A (80.37%) was obtained from a commercial source. The impurities (6.22% stevioside, 2.28% rebaudioside C, 0.35% dulcoside A, 0.78% rebaudioside F, 0.72% other steviol glycosides, 3.33% rebaudioside B, 0.07% steviolbioside) were identified and quantified by HPLC on a dry basis (moisture content 3.4%).

Crude rebaudioside A (100 g), ethanol (95%, 320 mL), methanol (99%, 120 mL) and water (50 mL) were combined and heated to 30-40° C. for 10 minutes. The clear solution was cooled to 22° C. for 16 hours. The white crystals were filtered and washed twice with ethanol (2×50 mL, 95%). The wet filter cake (88 g) was slurried in ethanol (95%, 1320 mL) for 16 hours, filtered, washed with ethanol (95%, 2×100 mL) and dried in a vacuum oven at 60° C. for 16-24 hours under reduced pressure (20 mm).

The final composition of substantially pure rebaudioside A (72 g) comprised 98.29% rebaudioside A, 0.03% stevioside, 0.02% rebaudioside C, 0.17% rebaudioside F, 0.06% rebaudioside D and 1.09% rebaudioside B. Steviolbioside was not detected by HPLC.

Example A3

Crude rebaudioside A (80.37%) was obtained from a commercial source. The impurities (6.22% stevioside, 2.28% rebaudioside C, 0.35% dulcoside A, 0.78% rebaudioside F, 0.72% other steviol glycosides, 3.33% rebaudioside B, 0.07% steviolbioside) were identified and quantified by HPLC on a dry basis (moisture content 3.4%).

Crude rebaudioside A (50 g), ethanol (95%, 160 mL), methanol (99%, 60 mL) and water (25 mL) were combined and heated to approximately 30° C. for 10 minutes. The clear solution was cooled to 22° C. for 16 hours. The white crystals were filtered and washed twice with ethanol (2×25 mL, 95%). The wet filter cake (40 g) was slurried in methanol (99%, 600 mL) for 16 hours, filtered, washed with methanol (99%, 2×25 mL) and dried in a vacuum oven at 60° C. for 16-24 hours under reduced pressure (20 mm).

The final composition of substantially pure rebaudioside A (27.3 g) comprised 98.22% rebaudioside A, 0.04% stevioside, 0.04% rebaudioside C, 0.18% rebaudioside F, 0.08% rebaudioside D) and 1.03% rebaudioside B. Steviolbioside was not detected by HPLC.

Example Set B

TABLE 4

Summary of Examples B1-19

| | Crude Rebaudioside A (g) | Solvent Ethanol (95%)(mL) | Organic Co-solvent (mL) | Water (mL) | Wash Solvent | HPLC Yield (g) | Purity (%) |
|---|---|---|---|---|---|---|---|
| B1 | 5 | 16 | Methanol (6) | 2 | EtOH/MeOH (4:1.5 v/v) | 3.2 | >97 |
| B2 | 5 | 16 | Methanol (4) | 2 | EtOH/MeOH (4:1 v/v) | 3.1 | >97 |
| B3 | 5 | 9.5 | 1-Butanol (9.5) | 1 | EtOH/1-Butanol (1:1 v/v) | 3.2 | >95 |
| B4 | 5 | 9.5 | 1-Butanol (9) | 1 | EtOH/MeOH (1:1 v/v) | 3.5 | >96 |
| B5 | 5 | 12.5 | Methanol (6) | 2 | *EtOH/MeOH (4:1 v/v) | 3.3 | >97 |
| B6 | 5 | 12.5 | Acetonitrile (6) | 1.5 | *EtOH/Acetonitrile (6:3 v/v) | 3.4 | >95 |
| B7 | 5 | 14.5 | Ethyl acetate (4) | 4 | *EtOH/Ethyl Acetate (7:2 v/v) | 3.4 | >95 |
| B8 | 5 | 16 | Methanol (6) | 2 | EtOH/MeOH (4:1.5 v/v) | 3.2 | >97 |
| B9 | 5 | 16 | Methanol (4) | 2 | EtOH/MeOH (4:1 v/v) | 3.1 | >97 |
| B10 | 5 | 14.5 | Methanol (4) | 1.5 | EtOH/MeOH (7:2 v/v) | 3.4 | >97 |
| B11 | 5 | 16 | Methanol (6) | 1.5 | EtOH/MeOH (8:3 v/v) | 3.2 | >97 |
| B12 | 5 | 16 | Methanol (6) | 2 | *EtOH/MeOH (8:3 v/v) | 3.2 | >96 |
| B13 | 5 | 16 | Methanol (6) | 2 | *EtOH/MeOH (8:3 v/v) | 3.4 | >96 |
| B14 | 5 | 15 | Methanol (5) | 2.5 | EtOH/MeOH (3:1 v/v) | 3.2 | >97 |
| B15 | 5 | 15 | Methanol (5) | 3 | EtOH/MeOH (3:1 v/v) | 2.7 | >97 |
| B16 | 5 | 15 | Methanol (6) | 3.5 | EtOH/MeOH (3:1 v/v) | 2.6 | >99 |
| B17 | 5 | 15 | Methanol (5) | 4 | EtOH/MeOH (3:1 v/v) | 2.3 | >99 |
| B18 | 5 | 16 | Methanol (6) | 2.5 | *EtOH/MeOH (8:3 v/v) | 3.0 | >97 |
| B19 | 5 | 16 | Methanol (6) | 2.5 | *EtOH/MeOH (8:3 v/v) | 3.2 | >98 |

Example B1

Crude rebaudioside A (77.4% purity, 5 g), ethanol (95%, 16 mL), methanol (6 mL) and water (2 mL) were combined and heated to reflux for 10 minutes. The clear solution was cooled to 22° C. for 16 hours. The white crystalline product was filtered, washed twice with ethanol:methanol (5 mL, 4:1.5, v/v) mixture and dried in a vacuum oven at 50° C. for 16-24 hours under reduced pressure (20 mm) to yield 3.2 g of purified product (>97% by HPLC).

Example B2

Crude rebaudioside A (77.4% purity, 5 g), ethanol (95%, 16 mL), methanol (4 mL) and water (2 mL) were combined and heated to reflux for 10 minutes. The clear solution was cooled to 22° C. for 16 hours. The white crystalline product was filtered, washed twice with ethanol:methanol (5 mL, 4:1, v/v) mixture and dried in a vacuum oven at 50° C. for 16-24 hours under reduced pressure (20 mm) to yield 3.1 g of purified product (>97% by HPLC).

Example B3

Crude rebaudioside A (77.4% purity, 5 g), ethanol (95%, 9.5 mL), 1-butanol (9.5 mL) and water (1 mL) were combined and heated to reflux for 10 minutes. The clear solution was cooled to 22° C. for 16 hours. The white crystalline product was filtered, washed twice with ethanol:1-butanol (5 mL, 1:1, v/v) mixture and dried in a vacuum oven at 50° C. for 16-24 hours under reduced pressure (20 mm) to yield 3.2 g of purified product (>95% by HPLC).

Example B4

Crude rebaudioside A (80.37% purity, 5 g), ethanol (95%, 9.5 mL), methanol (9 mL) and water (1 mL) were combined and heated to reflux for 10 minutes. The clear solution was cooled to 22° C. for 16 hours. The white crystalline product was filtered, washed twice with ethanol:methanol (5 mL, 1:1, v/v) mixture and dried in a vacuum oven at 50° C. for 16-24 hours under reduced pressure (20 mm) to yield 3.5 g of purified product (>96% by HPLC).

Example B5

Crude rebaudioside A (80.37% purity, 5 g), ethanol (95%, 12.5 mL), methanol (6 mL) and water (2 mL) were combined and heated to reflux for 10 minutes. The clear solution was cooled to 22° C. The solution was seeded with 10 mg of 98% pure rebaudioside A and the mixture was left at 22° C. for 16 hours. The white crystalline product was filtered, washed twice with ethanol-methanol (5 mL, 4:1, v/v) mixture and dried in a vacuum oven at 50° C. for 16-24 hours under reduced pressure (20 mm) to yield 3.3 g of purified product (>97% by HPLC).

Example B6

Crude rebaudioside A (80.37% purity, 5 g), ethanol (95%, 12.5 mL), acetonitrile (6 mL) and water (1.5 mL) were combined and heated to reflux for 10 minutes. The clear solution was cooled to 22° C. The solution was seeded with 10 mg of 98% pure rebaudioside A and the mixture was left at 22° C. for 16 hours. The white crystalline product was filtered, washed twice with ethanol:acetonitrile (5 mL, 6:3, v/v) mixture and dried in a vacuum oven at 50° C. for 16-24 hours under reduced pressure (20 mm) to yield 3.4 g of purified product (>95% by HPLC).

Example B7

Crude rebaudioside A (80.37% purity, 5 g), ethanol (95%, 14.5 mL), ethyl acetate (4 mL) and water (1.5 mL) were combined and heated to reflux for 10 minutes. The clear solution was cooled to 22° C. The solution was seeded with 10 mg of 98% pure rebaudioside A and the mixture was left at 22° C. for 16 hours. The white crystalline product was filtered, washed twice with ethanol:acetonitrile (5 mL, 7:2, v/v) mixture and dried in a vacuum oven at 50° C. for 16-24 hours under reduced pressure (20 mm) to yield 3.4 g of purified product (>95% by HPLC).

Example B8

Crude rebaudioside A (80.37% purity, 5 g), ethanol (95%, 16 mL), methanol (6 mL) and water (2 mL) were combined and heated to reflux for 10 minutes. The clear solution was cooled to 22° C. for 16 hours. The white crystalline product was filtered, washed twice with ethanol:methanol (5.5 mL, 4:1.5, v/v) mixture and dried in a vacuum oven at 50° C. for 16-24 hours under reduced pressure (20 mm) to yield 3.2 g of purified product (>97% by HPLC).

Example B9

Crude rebaudioside A (80.37% purity, 5 g), ethanol (95%, 16 mL), methanol (4 mL) and water (2 mL) were combined and heated to reflux for 10 minutes. The clear solution was cooled to 22° C. for 16 hours. The white crystalline product was filtered, washed twice with ethanol:methanol (5.0 mL, 4:1, v/v) mixture and dried in a vacuum oven at 50° C. for 16-24 hours under reduced pressure (20 mm) to yield 3.1 g of purified product (>97% by HPLC).

Example B10

Crude rebaudioside A (80.37% purity, 5 g), ethanol (95%, 14.5 mL), methanol (4 mL) and water (1.5 mL) were combined and heated to reflux for 10 minutes. The clear solution was cooled to 22° C. for 16 hours. The white crystalline product was filtered, washed twice with ethanol:methanol (5.0 mL, 7:2, v/v) mixture and dried in a vacuum oven at 50° C. for 16-24 hours under reduced pressure (20 mm) to yield 3.4 g of purified product (>97% by HPLC).

Example B11

Crude rebaudioside A (80.37% purity, 5 g), ethanol (95%, 16 mL), methanol (6 mL) and water (1.5 mL) were combined and heated to reflux for 10 minutes. The clear solution was cooled to 22° C. for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.2 g of purified product (>97% by HPLC).

Example B12

Crude rebaudioside A (80.37% purity, 5 g), ethanol (95%, 16 mL), methanol (6 mL) and water (2 mL) were combined and heated to reflux for 10 minutes. The clear solution was cooled to 22° C. and seeded with 10 mg of pure rebaudioside A (>98%). The mixture was kept at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.2 g of purified product (>98% by HPLC).

Example B13

Crude rebaudioside A (80.37% purity, 5 g), ethanol (95%, 16 mL), methanol (6 mL) and water (2 mL) were combined and heated to reflux for 10 minutes. The clear solution was cooled to 22° C. and seeded with 10 mg of pure rebaudioside A (>98%). The mixture was kept at room temperature for 16 hours while stirring. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.4 g of purified product (>96% by HPLC).

Example B14

Crude rebaudioside A (80.37% purity, 5 g), ethanol (95%, 15 mL), methanol (5 mL) and water (2.5 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 3.2 g of purified product (>97% by HPLC).

Example B15

Crude rebaudioside A (80.37% purity, 5 g), ethanol (95%, 15 mL), methanol (5 mL) and water (3.0 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.7 g of purified product (>97% by HPLC).

Example B16

Crude rebaudioside A (80.37% purity, 5 g), ethanol (95%, 15 mL), methanol (5 mL) and water (3.5 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.6 g of purified product (>99% by HPLC).

Example B17

Crude rebaudioside A (80.37% purity, 5 g), ethanol (95%, 15 mL), methanol (5 mL) and water (4.0 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.3 g of purified product (>99% by HPLC).

Example B18

Crude rebaudioside A (80.37% purity, 5 g), ethanol (95%, 16 mL), methanol (6 mL) and water (2.5 mL) were combined and heated to reflux for 10 minutes. The clear solution was cooled to 22° C. This mixture was stirred at room temperature for 15-30 minutes during which time crystals started to appear. The stirring was stopped and the mixture was kept at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.0 g of purified product (>97% by HPLC).

Example B19

Crude rebaudioside A (80.37% purity, 5 g), ethanol (95%, 16 mL), methanol (6 mL) and water (2.5 mL) were combined and heated to reflux for 10 minutes. The clear solution was cooled to 22° C. for 2 hours. During this time crystals started to appear. The mixture was stirred at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.2 g of purified product (>98% by HPLC).

Example Set C

TABLE 5

Summary of Examples C1-9

| | Crude Rebaudioside A (g) | Solvent | | | | | |
|---|---|---|---|---|---|---|---|
| | | Organic Solvent (mL) | Organic Co-solvent (mL) | Water (mL) | Wash Solvent | Yield (g) | HPLC Purity (%) |
| C1 | 5 | Isopropanol (9.5) | Methanol (9.5) | 1 | Isopropanol/MeOH (1:1 v/v) | 3.85 | >91 |
| C2 | 5 | sec-Butanol (9.5) | Methanol (9.5) | 1 | MeOH/sec-Butanol (1:1 v/v) | 4.0 | >91 |
| C3 | 5 | 1-Propanol (9.5) | Methanol (9.5) | 1 | MeOH/1-Propanol (1:1 v/v) | 3.55 | >91.2 |
| C4 | 5 | Ethanol (9.5) | 1-Propanol (9.5) | 1 | EtOH/1-Propanol (1:1 v/v) | 2.5 | >94 |
| C5 | 5 | 1-Butanol (9.5) | Methanol (9.5) | 1 | MeOH/1-Butanol (1:1 v/v) | 3.7 | >91.5 |
| C6 | 5 | Ethanol (9.5) | 2-Propanol (9.5) | 1 | EtOH/2-Propanol (1:1 v/v) | 2.4 | >93.5 |
| C7 | 5 | Ethanol (9.5) | sec-Butanol (9.5) | 1 | EtOH/sec-Butanol (1:1 v/v) | 2.9 | >93 |

TABLE 5-continued

Summary of Examples C1-9

| | Crude Rebaudioside A (g) | Organic Solvent (mL) | Organic Co-solvent (mL) | Water (mL) | Wash Solvent | Yield (g) | HPLC Purity (%) |
|---|---|---|---|---|---|---|---|
| C8 | 5 | tert-Butanol (9.5) | Methanol (9.5) | 1 | MeOH/tert-Butanol (1:1 v/v) | 3.9 | >83 |
| C9 | 5 | Ethanol (9.5) | tert-Butanol (9.5) | 1 | EtOH/tert-Butanol (1:1 v/v) | 2.9 | >88 |

Example C1

Crude rebaudioside A (80.37% purity, 5 g), methanol (99%, 9.5 mL), isopropanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with an ethanol:methanol (5.0 mL, 8:3, v/v) mixture and dried in a vacuum oven at 50° C. for 16-24 hours under reduced pressure (20 mm) to yield 3.85 g of purified product (>91.0% by HPLC).

Example C2

Crude rebaudioside A (80.37% purity, 5 g), methanol (99%, 9.5 mL), sec-butanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with a methanol: sec-butanol (10.0 mL, 1:1, v/v) mixture and dried in a vacuum oven at 50° C. for 16-24 hours under reduced pressure (20 mm) to yield 4.0 g of purified product (>91.0% by HPLC).

Example C3

Crude rebaudioside A (80.37% purity, 5 g), methanol (99%, 9.5 mL), 1-propanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with a methanol: 1-propanol (10.0 mL, 1:1, v/v) mixture and dried in a vacuum oven at 50° C. for 16-24 hours under reduced pressure (20 mm) to yield 3.55 g of purified product (>91.21% by HPLC).

Example C4

Crude rebaudioside A (80.37% purity, 5 g), ethanol (95%, 9.5 mL), 1-propanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with an ethanol: 1-propanol (10.0 mL, 1:1, v/v) mixture and dried in a vacuum oven at 50° C. for 16-24 hours under reduced pressure (20 mm) to yield 2.5 g of purified product (>94.0% by HPLC).

Example C5

Crude rebaudioside A (80.37% purity, 5 g), methanol (99%, 9.5 mL), 1-butanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with a methanol: 1-butanol (10.0 mL, 1:1, v/v) mixture and dried in a vacuum oven at 50° C. for 16-24 hours under reduced pressure (20 mm) to yield 3.7 g of purified product (>91.5% by HPLC).

Example C6

Crude rebaudioside A (80.37% purity, 5 g), ethanol (95%, 9.5 mL), 2-propanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with an ethanol: 2-propanol (10.0 mL, 1:1, v/v) mixture and dried in a vacuum oven at 50° C. for 16-24 hours under reduced pressure (20 mm) to yield 2.4 g of purified product (>93.5% by HPLC).

Example C7

Crude rebaudioside A (77.4% purity, 5 g), ethanol (95%, 9.5 mL), sec-butanol (9.5 mL) and water (1 mL) were combined and heated to reflux for 10 minutes. The clear solution was cooled to 22° C. for 2 hours and then stirred at room temperature for 16 hours. The white crystalline product was filtered, washed twice with an ethanol: sec-butanol (10.0 mL, 1:1, v/v) mixture and dried in a vacuum oven at 50° C. for 16-24 hours under reduced pressure (20 mm) to yield 2.9 g of purified product (>93.0% by HPLC).

Example C8

Crude rebaudioside A (77.4% purity, 5 g), methanol (99%, 9.5 mL), tert-butanol (9.5 mL) and water (1 mL) were combined and heated to about 40-50° C. for 10 minutes. The clear solution was cooled to 22° C. for 2 hours and then stirred at room temperature for 16 hours. The white crystalline product was filtered, washed twice with methanol (99%, 7.0 mL) and dried in a vacuum oven at 50° C. for 16-24 hours under reduced pressure (20 mm) to yield 3.9 g of purified product (>83.0% by HPLC).

Example C9

Crude rebaudioside A (77.4% purity, 5 g), ethanol (95%, 9.5 mL), tert-butanol (9.5 mL) and water (1 mL) were combined and heated to reflux for 10 minutes. The clear solution was cooled to 22° C. for 2 hours and then stirred at room temperature for 16 hours. The white crystalline product was filtered, washed twice with ethanol (95%, 7.0 mL) and dried in a vacuum oven at 50° C. for 16-24 hours under reduced pressure (20 mm) to yield 2.9 g of purified product (>88.0% by HPLC).

Example Set D

TABLE 6

Summary of Examples D1-12

| | Crude Rebaudioside A (g) | Solvent Organic Solvent (mL) | Water (mL) | Wash Solvent | Yield (g) | HPLC Purity (%) |
|---|---|---|---|---|---|---|
| D1 | 50 | MeOH (180) | 20 | MeOH | 29.8 | 96.2 |
| D2 | 50 | MeOH (160) | 40 | MeOH | 31.2 | 95.5 |
| D3 | 50 | EtOH (188) | 12 | EtOH | 37.3 | 93.4 |
| D4 | 50 | EtOH (184) | 16 | EtOH | 31.7 | 95.3 |
| D5 | 50 | EtOH (180) | 10 | EtOH | 35.7 | 94.7 |
| D6 | 50 | EtOH (176) | 24 | EtOH | 38.2 | 97.3 |
| D7 | 50 | EtOH (172) | 28 | EtOH | 32 | 98.1 |
| D8 | 50 | EtOH (160) | 40 | EtOH | 19.8 | 99.5 |
| D9 | 50 | 1-Propanol (180) | 20 | 1-Propanol | 27 | 92.9 |
| D10 | 50 | 2-Propanol (180) | 20 | 2-Propanol | 34.9 | 91.4 |
| D11 | 50 | 1-Butanol (180) | 20 | 1-Butanol | 40.6 | 93.1 |
| D12 | 50 | 2-Butanol (180) | 20 | 2-Butanol | 40.4 | 90.5 |

Example D1

Crude rebaudioside A (77.4% purity, 50 g), methanol (99%, 180 mL) and water (20 mL) were combined and heated to reflux for 30 minutes. The mixture was then allowed to cool to ambient temperature for 16-24 hours. The white crystalline product was filtered, washed twice with methanol (99%, 25 mL), and dried in a vacuum oven at 60° C. for 16-24 hours under reduced pressure (20 mm) to yield 29.8 g of purified product (96.2% by HPLC).

Example D2

Crude rebaudioside A (80.37% purity, 50 g), methanol (99%, 160 mL) and water (40 mL) were combined and heated to reflux for 30 minutes. The mixture was then allowed to cool to ambient temperature for 1 week. The white crystalline product was filtered, washed twice with methanol (99%, 25 mL), and dried in a vacuum oven at 60° C. for 16-24 hours under reduced pressure (20 mm) to yield 31.2 g of purified product (95.5% by HPLC).

Example D3

Crude rebaudioside A (80.37% purity, 50 g), ethanol (95%, 188 mL) and water (12 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 37.3 g of purified product (93.4% by HPLC).

Example D4

Crude rebaudioside A (80.37% purity, 50 g), ethanol (95%, 184 mL) and water (16 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 31.7 g of purified product (95.3% by HPLC).

Example D5

Crude rebaudioside A (80.37% purity, 50 g), ethanol (95%, 180 mL) and water (20 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 35.7 g of purified product (94.7% by HPLC).

Example D6

Crude rebaudioside A (80.37% purity, 50 g), ethanol (95%, 176 mL) and water (24 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 38.2 g of purified product (97.3% by HPLC).

Example D7

Crude rebaudioside A (80.37% purity, 50 g), ethanol (95%, 172 mL) and water (28 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 32.0 g of purified product (98.1% by HPLC).

Example D8

Crude rebaudioside A (80.37% purity, 50 g), ethanol (95%, 160 mL) and water (40 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 19.8 g of purified product (99.5% by HPLC).

Example D9

Crude rebaudioside A (80.37% purity, 50 g), 1-propanol (180 mL) and water (20 mL) were combined and heated to reflux for 30 minutes. The mixture was then allowed to cool to ambient temperature for 16-24 hours. The white crystalline product was filtered, washed twice with 1-propanol (25 mL), and dried in a vacuum oven at 60° C. for 16-24 hours under reduced pressure (20 mm) to yield 27.0 g of purified product (92.9% by HPLC).

Example D10

Crude rebaudioside A (80-37% purity, 50 g), 2-propanol (180 mL) and water (20 mL) were combined and heated to reflux for 30 minutes. The mixture was then allowed to cool to ambient temperature for 16-24 hours. The white crystalline product was filtered, washed twice with 2-propanol (25 mL), and dried in a vacuum oven at 60° C. for 16-24 hours under reduced pressure (20 mm) to yield 34.9 g of purified product (91.4% by HPLC).

Example D11

Crude rebaudioside A (80.37% purity, 50 g), 1-butanol (180 mL) and water (20 mL) were combined and heated to reflux for 30 minutes. The mixture was then allowed to cool to ambient temperature for 16-24 hours. The white crystalline product was filtered, washed twice with 1-butanol (25 mL), and dried in a vacuum oven at 60° C. for 16-24 hours under reduced pressure (20 mm) to yield 40.6 g of purified product (93.1% by HPLC).

Example D12

Crude rebaudioside A (80.37% purity, 50 g), 2-butanol (180 mL) and water (20 mL) were combined and heated to reflux for 30 minutes. The mixture was then allowed to cool to ambient temperature for 16-24 hours. The white crystalline product was filtered, washed twice with 2-butanol (25 mL), and dried in a vacuum oven at 60° C. for 16-24 hours under reduced pressure (20 mm) to yield 40.4 g of purified product (90.5% by HPLC).

Example Set E

TABLE 7

Summary of Examples E1-E3

|    | Crude Rebaudioside A (g) | Ethanol (95%)(mL) | Organic Co-solvent (mL) | Water (mL) | Methanol Slurry (mL) | Yield (g) | HPLC Purity (%) |
|----|---|---|---|---|---|---|---|
| E1 | 50 | 160 | Methanol (60) | 25 | 200 | 12.7 | >97 |
| E2 | 50 | 160 | Methanol (60) | 25 | 300 | 18.6 | >97 |
| E3 | 50 | 160 | Methanol (60) | 25 | 350 | 22.2 | >97 |

Example E1

Crude rebaudioside A (41% purity, 50 g), ethanol (95%, 160 mL), methanol (99.8%, 60 mL) and water (25 mL) were combined by stirring at 22° C. A white product crystallized out in 5-20 hours. The mixture was stirred for additional 48 hours. The white crystalline product was filtered and washed twice with ethanol (95%, 25 mL). The wet cake of white crystalline product then was slurried in methanol (99.8%, 200 mL) for 16 hours, filtered, washed twice with methanol (99.8%, 25 mL), and dried in a vacuum oven at 60° C. for 16-24 hours under reduced pressure (20 mm) to yield 12.7 g of purified product (>97% by HPLC).

Example E2

Crude rebaudioside A (48% purity, 50 g), ethanol (95%, 160 mL), methanol (99.8%, 60 mL) and water (25 mL) was combined by stirring at 22° C. The white product crystallized out in 3-6 hours. The mixture was stirred for additional 48 hours. The white crystalline product was filtered and washed twice with ethanol (95%, 25 mL). The wet cake of white crystalline product then was slurried in methanol (99.8% 300 mL) for 16 hours, filtered, washed twice with methanol (99.8%, 25 mL) and dried in a vacuum oven at 60° C. for 16-24 hours under reduced pressure (20 mm) to yield 18.6 g of purified product (>97% by HPLC).

Example E3

Crude rebaudioside A (55% purity, 50 g), ethanol (95%, 160 mL), methanol (99.8%, 60 mL) and water (25 mL) was combined by stirring at 22° C. The white product crystallized out in 15-30 minutes. The mixture was stirred for an additional 48 hours. The white crystalline product was filtered and washed twice with ethanol (95%, 25 mL). The wet cake of white crystalline product was slurried in methanol (99.8%, 350 mL) for 16 hours, filtered, washed twice with methanol (99.8%, 25 mL) and dried in a vacuum oven at 60° C. for 16-24 hours under reduced pressure (20 mm) to yield 22.2 g of purified product (>97% by HPLC).

Example F

A solution of substantially pure rebaudioside A obtained using the purification technique described hereinabove (>97% pure by HPLC) was prepared in double distilled water (12.5 gm in 50 mL, 25% concentration) by stirring the mixture at 40° C. for 5 minutes. An amorphous form of rebaudioside A was formed by immediately using the clear solution for spray drying with the Lab-Plant spray drier SD-04 instrument (Lab-Plant Ltd., West Yorkshire, U.K.). The solution was fed through the feed pump into the nozzle atomizer, which atomized the rebaudioside A solution into a spray of droplets with the help of a constant flow of nitrogen/air. Moisture was evaporated from the droplets under controlled temperature conditions (about 90 to about 97° C.) and airflow conditions in the drying chamber and resulted in the formation of dry particles. This dry powder (11-12 g, $H_2O$ 6.74%)

was discharged continuously from the drying chamber and was collected in a bottle. The rate of dissolution in water at room temperature was determined to be >35.0%.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A method for purifying polymorphic and/or amorphous forms of rebaudioside A comprising the steps of:
    combining a crude rebaudioside A mixture containing an extract from *Stevia* plants with an aqueous organic solvent to form a rebaudioside A solution,
    wherein the crude rebaudioside A mixture contains rebaudioside A in a purity from about 60% to about 85%, the aqueous organic solvent and the crude rebaudioside A mixture are present in the rebaudioside A solution in a weight ratio from about 4 to about 10 parts aqueous organic solvent to about 1 part crude rebaudioside A, and the aqueous organic solvent contains water in an amount from about 10% to about 25% by weight, and a mixture of ethanol and methanol;
    heating the rebaudioside A solution at a temperature in a range from room temperature to about 40° C.;
    crystallizing the rebaudioside A solution in a single crystallization step to provide a substantially pure rebaudioside A composition; and
    separating and washing the substantially pure rebaudioside A composition to provide rebaudioside A in a purity greater than 95% by weight on a dry basis.

2. The method of claim 1, wherein the crude rebaudioside A mixture contains rebaudioside A in a purity from about 70% to about 85% by weight.

3. The method of claim 1, wherein the aqueous organic solvent and the crude rebaudioside A mixture are present in the rebaudioside A solution in a weight ratio from about 3 to about 5 parts aqueous organic solvent to about 1 part crude rebaudioside A.

4. The method of claim 1, wherein the water content of the aqueous organic solvent ranges from about 15% to about 20% by weight.

5. The method of claim 1, wherein the ethanol and methanol are present in the aqueous organic solution in a weight ratio from about 20 parts to about 1 part ethanol to about 1 part methanol.

6. The method of claim 1, wherein the ethanol and methanol are present in the aqueous organic solution in a weight ratio from about 3 parts to about 1 part ethanol to about 1 part methanol.

7. The method of claim 1, further comprising the step of cooling the rebaudioside A solution after the heating step.

8. The method of claim 7, wherein the step of cooling the rebaudioside A solution comprises cooling the rebaudioside A solution for about 0.5 hours to about 24 hours.

9. The method of claim 1, further comprising the step of drying the rebaudioside A having a purity greater than 95% by weight on a dry basis, wherein an anhydrous form of rebaudioside A results with drying.

10. The method of claim 1, further comprising the steps of:
    cooling the rebaudioside A solution after the heating step; and
    drying the rebaudioside A having a purity greater than 95% by weight on a dry basis.

11. The method of claim 1, wherein the rebaudioside A solution in the single crystallization step is stirred or unstirred.

12. The method of claim 1, wherein the crude rebaudioside A contains substantially no rebaudioside D impurity, and the method further comprises slurrying the substantially pure rebaudioside A composition in an aqueous organic solvent or in an organic solvent.

13. The method of claim 1, wherein the purity of rebaudioside A is greater than 97% by weight on a dry basis.

14. The method of claim 1, wherein the purity of rebaudioside A is greater than 98% by weight on a dry basis.

15. The method of claim 1, wherein the purity of rebaudioside A is greater than 99% by weight on a dry basis.

* * * * *